United States Patent

Hamprecht et al.

Patent Number: 5,276,007
Date of Patent: Jan. 4, 1994

[54] HERBICIDAL SULFONYLUREAS

[75] Inventors: Gerhard Hamprecht, Weinheim; Horst Mayer, Ludwigshafen; Karl-Otto Westphalen, Speyer; Bruno Wuerzer, Otterstadt; Matthias Gerber, Mutterstadt; Klaus Grossmann; Wilhelm Rademacher, both of Limburgerhof, all of Fed. Rep. of Germany

[73] Assignee: BASF Aktiengesellschaft, Ludwigshafen, Fed. Rep. of Germany

[21] Appl. No.: 656,912

[22] Filed: Feb. 19, 1991

[30] Foreign Application Priority Data

Mar. 10, 1990 [DE] Fed. Rep. of Germany ........ 4007683

[51] Int. Cl.$^5$ .................... C07D 239/69; A01N 43/54
[52] U.S. Cl. ........................... 504/214; 544/123; 544/321; 504/215; 504/219; 504/225; 504/242; 504/243; 540/601
[58] Field of Search .................... 71/92; 544/321, 123; 504/219, 225, 242, 243, 214, 215; 540/601

[56] References Cited

U.S. PATENT DOCUMENTS

| | | | |
|---|---|---|---|
| 4,478,635 | 10/1984 | Meyer et al. | 544/321 |
| 4,518,776 | 5/1985 | Meyer et al. | 544/321 |
| 4,547,215 | 10/1985 | Wolf et al. | 71/92 |
| 4,551,531 | 11/1985 | Meyer et al. | 544/320 |
| 4,592,978 | 6/1986 | Levitt | 544/321 |
| 4,643,760 | 2/1987 | Meyer et al. | 544/320 |
| 4,831,138 | 5/1989 | Lachhein | 544/320 |

FOREIGN PATENT DOCUMENTS 1223591 6/1987 Canada.
084020 7/1983 European Pat. Off..

OTHER PUBLICATIONS

Chemical Abstracts, vol. 109, entry 88185s (1988).

Primary Examiner—John M. Ford
Attorney, Agent, or Firm—Keil & Weinkauf

[57] ABSTRACT

Substituted sulfonylureas of the general formula I

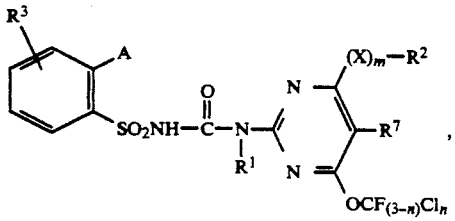

where n and m are each 0 or 1, and
$R^1$ is hydrogen, alkyl, alkenyl or alkynyl;
$R^2$ is halogen or trifluoromethyl when m is 0, or, when m is 1, alkyl, alkenyl or alkynyl and, when X is O or S and m is 1, is trifluoromethyl or chlorodifluoromethyl;
X is O, S or N—$R^4$, where $R^4$ is hydrogen or alkyl;
$R^3$ is hydrogen, halogen, alkyl, haloalkyl or alkoxy;
A is haloalkyl, halogen or

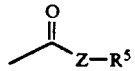

where Z is oxygen or alkylimino N—$R^6$;
$R^5$ is hydrogen, substituted or unsubstituted alkyl, substituted or unsubstituted cycloalkyl, alkenyl or alkynyl;
$R^6$ is hydrogen, alkyl, or together with $R^5$ is a $C_4$-$C_6$-alkylene chain, where one methylene may be replaced by an oxygen atom or a $C_1$-$C_4$-alkylimino group, and
$R^7$ is hydrogen or halogen, and environmentally tolerated salts thereof, processes and intermediates for the manufacture of compounds I, and their use as herbicides and bioregulators.

5 Claims, No Drawings

HERBICIDAL SULFONYLUREAS

The present invention relates to substituted sulfonylureas of the formula I

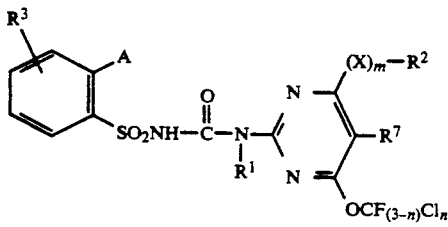

where
n and m are each 0 or 1, and
$R^1$ is hydrogen, $C_1$-$C_4$-alkyl, $C_3$-$C_6$-alkenyl or $C_3$-$C_6$-alkynyl,
$R^2$ is halogen or trifluoromethyl when m is 0, or $C_1$-$C_4$-alkyl, $C_3$-$C_6$-alkenyl or $C_3$-$C_6$-alkynyl when m is 1, or trifluoromethyl or chlorodifluoromethyl when X is O or S and m is 1,
X is O, S or N—$R^4$ where $R^4$ is hydrogen or $C_1$-$C_4$-alkyl,
$R^3$ is hydrogen, halogen, $C_1$-$C_4$-alkyl, $C_1$-$C_4$-haloalkyl or $C_1$-$C_4$-alkoxy,
A is $C_1$-$C_4$-haloalkyl, halogen or

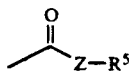

where
Z is oxygen or alkylimino $NR^6$,
$R^5$ is hydrogen, $C_1$-$C_6$-alkyl which can carry up to three of the following: halogen, $C_1$-$C_4$-alkoxyl $C_1$-$C_4$-alkylthio, $C_1$-$C_4$-haloalkoxy, $C_1$-$C_4$-alkoxy-$C_1$-$C_2$-alkoxy, $C_3$-$C_7$-cycloalkyl and/or phenyl, or $C_5$-$C_7$-cycloalkyl which can carry up to three $C_1$-$C_4$-alkyl groups, or $C_3$-$C_6$-alkenyl or $C_3$-$C_6$-alkynyl,
$R^6$ is hydrogen, $C_1$-$C_6$-alkyl, or together with $R^5$ is $C_4$-$C_6$-alkylene in which one methylene can be replaced by oxygen or $C_1$-$C_4$-alkylimino,
$R^7$ is hydrogen or halogen.

The present invention also relates to a process for preparing the compounds I and to the use thereof as herbicides and intermediates for preparing sulfonylureas I.

U.S. Pat. No. 4,547,215 discloses various sulfonylpyrimidylureas which are substituted by chlorine in the pyrimidine moiety as herbicides. EP-A-84,020 and 169,815 describe sulfonylureas which are substituted in the pyrimidine moiety by difluoromethoxy or bromodifluoromethoxy. However, these compounds are unsatisfactory because the selectivity for noxious plants is inadequate.

It is an object of the present invention to provide novel sulfonylpyrimidylureas with improved herbicidal properties. We have found that this object is achieved by the sulfonylureas defined in the introduction.

We have also found that the compounds of the formula I and their alkali metal and alkaline earth metal salts act highly selectively against noxious plants in crops such as cereals and corn.

We have also found chemically original processes for preparing the compounds I. Unexpectedly by comparison with the prior art, the sulfonylureas I can be prepared regioselectively and in high yield and purity starting from substituted 2-amino-4-fluoroalkoxypyrimidines of the formula IIIa

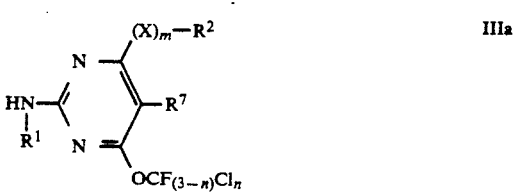

where
m is 1 and n is 0 or 1, and
$R^1$ is hydrogen, $C_1$-$C_4$-alkyl, $C_3$-$C_6$-alkenyl or $C_3$-$C_6$-alkynyl,
$R^2$ is $C_1$-$C_4$-alkyl, $C_3$-$C_6$-alkenyl or $C_3$-$C_6$-alkynyl,
$R^7$ is hydrogen or halogen,
X is O, S or N—$R^4$ where
$R^4$ is hydrogen or $C_1$-$C_4$-alkyl.

The present invention also relates to these intermediates and the preparation thereof.

The preparation of compounds which are halogen-substituted in the pyrimidine moiety ($R^2$=Hal, m=0) starts from appropriately substituted 2-amino-4-fluoroalkoxy-6-halopyrimidines of the structure IIIb (see scheme 2) to whose preparation the application U.S. Ser. No. 07/663,975, filed Mar. 4, 1991 relates. Pyrimidine intermediates with m=0 and $R^2$=trifluoromethyl are obtained in a similar manner as shown in scheme 3.

The sulfonylureas of the formula I according to the invention can be obtained by routes A, B and C shown in scheme 1:

A:

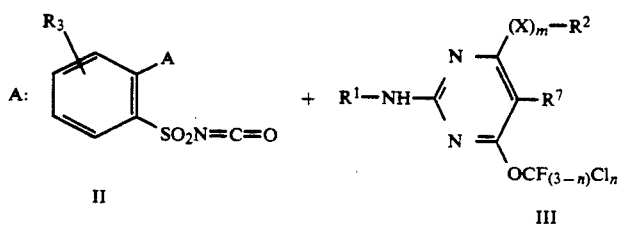

-continued

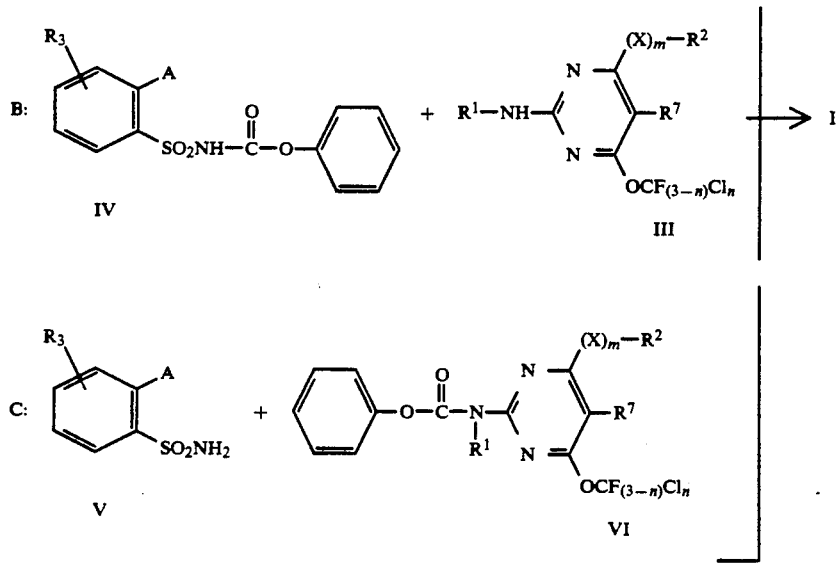

EMBODIMENT A

A sulfonyl isocyanate II is reacted in a conventional manner (EP-A-162,723) in an inert organic solvent with approximately the stoichiometric amount of a 2-aminopyrimidine III at from 0° to 120° C., preferably 10° to 100° C. The reaction can be carried out under atmospheric or superatmospheric (up to 50 bar) pressure, preferably under 1 to 5 bar, continuously or batchwise. Suitable solvents are listed in the abovementioned literature.

EMBODIMENT B

An appropriate sulfonylcarbamate of the formula IV is reacted in a conventional manner (EP-A-162,723) in an inert organic solvent at from 0° to 120° C., preferably 10° to 100° C., with a 2-aminopyrimidine. It is possible to add bases such as tertiary amines to increase the reaction rate and improve the product quality.

Examples of bases suitable for this purpose are tertiary amines such as pyridine, the picolines, 2,4- and 2,6-lutidine, 2,4,6-collidine, p-dimethylaminopyridine, 1,4-diaza[2.2.2]bicyclooctane (DABCO) and 1,8-diazabicyclo[5.4.0]undec-7-ene.

The solvents which are expediently used are those indicated in the literature and/or halohydrocarbons such as dichloromethane and chlorobenzene, ethers such as diethyl ether, tetrahydrofuran and dioxane, acetonitrile, dimethylformamide and/or ethyl acetate, in an amount of from 100 to 4000% by weight, preferably from 1000 to 2000% by weight, based on the starting materials II, IV and V.

For the purpose of preparing the compounds according to the invention, the 2-aminopyrimidine intermediates III can be obtained in the following advantageous manner:

Scheme 2

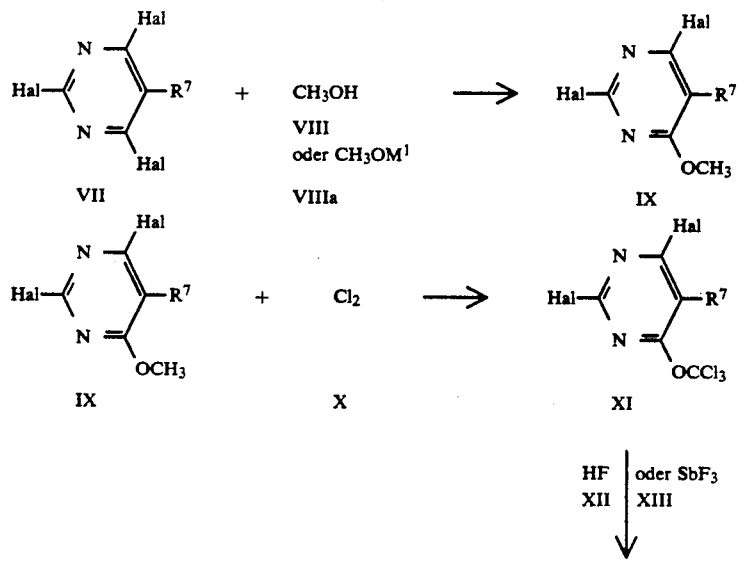

Scheme 2

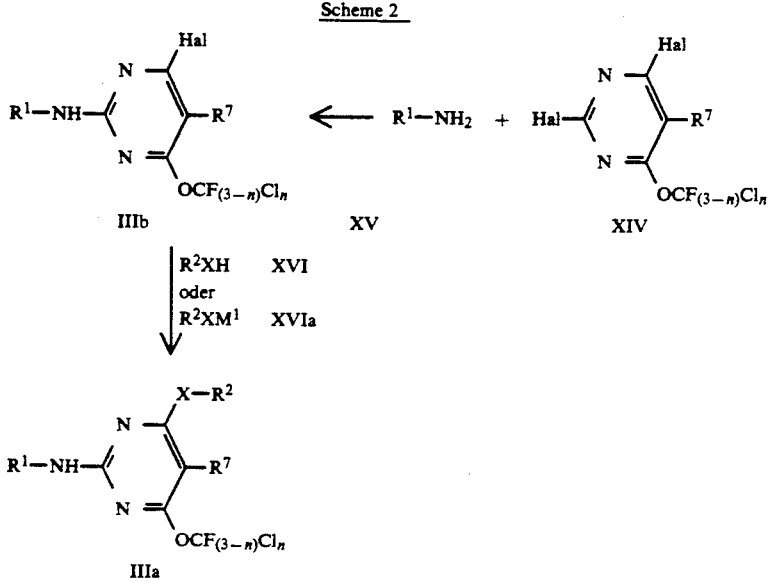

The 2-amino-6-trifluoromethylpyrimidine derivatives IIIc are obtained in a corresponding manner when the appropriate 2,4-dihalo-6-trichloromethylpyrimidines are reacted, in place of the 2,4,6-trihalo compounds VII, as shown in Scheme 3 (see Examples I.1, I.6 and I.12).

Scheme 3

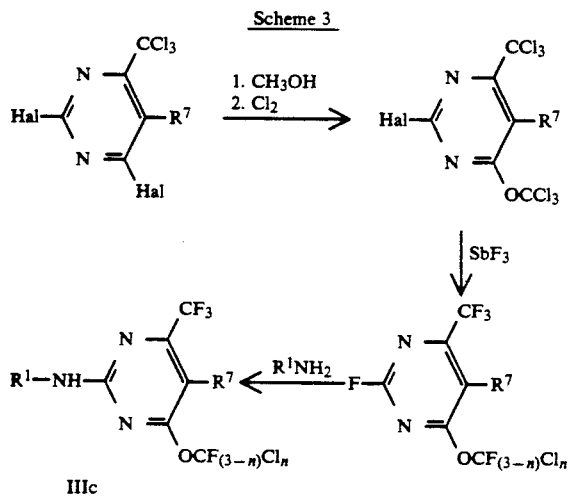

The intermediates IIId

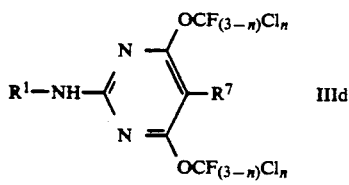

are obtained from the intermediates XIV in Scheme 2 by replacement of the 4-halogen atom by the reaction sequence depicted in Scheme 3 (1. $CH_3OH$, 2. $Cl_2$, 3. $SbF_3$) and subsequent reaction with $R^1NH_2$.

As shown in Scheme 2, for example, a 2,4,6-trihalopyrimidine VII, disclosed in J.Med.Chem. 6 (1963) 688, or commercially available, can be reacted in an aprotic polar solvent a) with methanol VIII in the presence or absence of a base or b) with a methanolate VIIIa in the presence of methanol VIII at from $-40°$ to $120°$ C. to give the methoxypyrimidine IX. These reactions can be carried out under atmospheric or superatmospheric (1 to 10 bar, preferably 1 to 5 bar) pressure, continuously or batchwise.

Hal in formula VII is fluorine, chlorine or bromine.

$M^1$ in formula VIIIa is a cation of an alkali metal such as lithium, sodium or potassium, or the equivalent of an alkaline earth metal cation such as magnesium, calcium or barium.

The following solvents are suitable for reacting the trihalopyrimidine with methanol VIII:

Ethers such as methyl tert.-butyl ether, diethyl ether, ethyl propyl ether, n-butyl ethyl ether, di-n-butyl ether, diisobutyl ether, diisoamyl ether, diisopropyl ether, cyclohexyl methyl ether, tetrahydrofuran, 1,2-dimethoxyethane, diethylene glycol dimethyl ether and anisole, chlorohydrocarbons such as 1,1,2,2-tetrachloroethane, 1,1-dichloroethylene, chlorobenzene, 1,2-dichlorobenzene and 1-chloronaphthalene, and mixtures thereof.

The solvent is expediently used in an amount of from 100 to 2000% by weight, preferably 500 to 1500% by weight, based on the starting material VII.

However, the reaction of the starting materials VII and VIII is expediently carried out directly in excess methanol VIII as solvent. It is possible to add an alkali metal methanolate VIIIa in an equivalent amount or in an amount which is up to 5 mol % above or below this, based on the starting material VII, to a suspension of the starting material VII in from 5 to 20 times the amount by weight of alcohol VIII as solvent, based on the starting material VII, over the course of up to one hour at from about $-20°$ to $80°$ C. To complete the reaction, the mixture is then stirred at from $0°$ to $120°$ C., preferably $0°$ to $100°$ C., for about ½ to 8 hours.

The methoxypyrimidines are isolated by conventional working up methods.

The methoxypyrimidine IX is chlorinated to give the trichloromethoxypyrimidine XI at, for example, from 60° to 180° C.

Suitable chlorinating agents are elemental chlorine and substances which release chlorine such as sulfuryl chloride or phosphorus pentachloride. It is also possible to generate chlorine in situ by oxidizing hydrochloric acid, for example with pyrolusite or by anodic chlorination.

The chlorination can be carried out in the presence of an inert solvent, for example a chlorohydrocarbon such as chloroform, tetrachloromethane, chlorobenzene, 1,2- or 1,3- or 1,4-dichlorobenzene, a nitrile such as acetonitrile or propionitrile, a nitro compound such as nitrobenzene, a carboxylic acid such as acetic or propionic acid, an anhydride such as acetic anhydride, an acid chloride such as chloroacetyl chloride, α-chloropropionyl chloride or α,α-dichloropropionyl chloride, an inorganic acid halide such as phosphorus trichloride or phosphorus oxychloride or, preferably, without solvent in the melt of the starting material IX.

A radical initiator can be used to increase the reaction rate; suitable for this is irradiation with light, preferably UV light, or addition of α,α'-azoisobutyronitrile, expediently in an amount of from 0.2 to 7 mol % based on the starting material IX. The reaction rate can also be increased by addition of a catalyst; suitable for this is phosphorus pentachloride, expediently in an amount of from 0.5 to 7 mol % based on the starting material IX. In this case, the starting material IX is mixed with the catalyst and then the chlorination is started. In place of phosphorus pentachloride, it is also possible to add components which form it under the reaction conditions, e.g. phosphorus trichloride or yellow phosphorus, and then to start with the chlorination.

Starting material IX can be reacted with chlorine in approximately stoichiometric amount or, preferably, in excess, advantageously with from 3.1 to 11, in particular 3.3 to 5, moles of $Cl_2$ per methoxy equivalent in the starting material IX. The reaction can be carried out at from 60° to 180° C., advantageously from 100° to 150° C., under atmospheric or superatmospheric pressure continuously or batchwise.

When chlorination is carried out under 1 bar, it is expedient to employ from 3.3 to 5 moles of chlorine gas based on one methoxy equivalent in the starting material IX, which corresponds to a chlorine conversion of from 91 to 60%. It is possible, by suitable measures, e.g. by use of moderate superatmospheric pressure, expediently from 1 to 10 bar, or by use of a bubble column, to increase the chlorine conversion. It is advantageous to maximize the time during which the chlorine gas is in contact with the organic phase by, for example, vigorously stirring the latter or forcing the chlorine gas to pass through a thick layer of the organic phase.

The reaction time is generally from about 0.5 to 12 hours.

The procedure in a preferred embodiment of the process is to pass the required amount of chlorine gas over the course of from 0.5 to 12 hours, preferably 1 to 10 hours, into the vigorously stirred liquid starting material IX, starting at from 60° to 80° C. and increasing the temperature continuously, possibly by utilizing the exothermic nature of the reaction, to from 100° to 150° C. at the end of the reaction. In the case of large batches, the exothermic nature of the reaction must be taken into account by applying external cooling or by suitable metering in of the chlorine; when the reaction subsides the cooling bath is removed and the mixture may then be heated.

The final products are worked up and isolated in a conventional manner. For example, residual hydrogen chloride, chlorine or catalyst can be driven out of the hot organic phase using an inert gas; this results in a high yield of a reasonably pure crude product. It can be further purified by distillation or chromatography or else employed immediately for further reactions.

The reaction of the trichloromethoxypyrimidine XI with a fluorinating agent is carried out at from 0° to 170° C., for example.

Suitable fluorinating agents are antimony trifluoride in the presence or absence of catalytic amounts of an antimony(V) salt, e.g. antimony(V) chloride, and hydrogen fluoride.

It is expedient to use an excess of from 1 to 200, preferably 5 to 20, mol % of antimony trifluoride per trichloromethyl equivalent. The amount of antimony(V) salt catalyst is from 1 to 20, preferably 5 to 18, mol % per trichloromethyl equivalent. The starting material XI is preferably metered at from 90° to 130° C. into the mixture containing the fluorinating agent, which is then heated at from 140° to 170° C. for from 10 to about 120 minutes. Working up is then carried out by distillation.

However, the reaction can also be carried out continuously by adding the starting material XI at from 140° to 170° C. over the course of from 10 to about 120 minutes and simultaneously distilling out under reduced pressure the lower boiling final product XIV. Traces of antimony salts which have been carried over can be removed by extraction with concentrated hydrochloric acid.

Halogen replacement can be stopped at the chlorodifluoromethoxy stage by using only small amounts, e.g. from 0.2 to 1 mol %, of antimony(V) salt catalyst, or none at all, and reducing the amount of antimony trifluoride to from 60 to 90 mol % per trichloromethyl equivalent.

In place of antimony trifluoride it is possible to use hydrogen fluoride at from 0° to 170° C., preferably 40° to 120° C. This is carried out by mixing the starting material XI with an excess of from 300 to 700, preferably 350 to 400, mol % hydrogen fluoride per trichloromethyl equivalent in an autoclave and stirring for from 10 minutes to about 10 hours. After the pressure has been released and volatiles have been removed, working up is carried out as described.

The reaction of the fluoromethoxypyrimidine XIV with an amine XV is carried out, for example, at from −80° to 40° C.

$R^1$ in formula XV is, for example, hydrogen, $C_1-C_4$-alkyl such as methyl, ethyl, n-propyl, i-propyl, n-butyl, sec.-butyl, i-butyl or tert.-butyl, $C_3-C_4$-alkenyl such as 2-propenyl, 2-methylethenyl, 2-butenyl, 3-butenyl, 1-methyl-2-propenyl or 2-methyl-2-propenyl, or $C_3-C_4$-alkynyl such as propargyl, 2-butynyl, 3-butynyl or 1-methyl-2-propynyl.

Among the amines which can be employed, the following may be mentioned: ammonia, methylamine, ethylamine, n-propylamine, isopropylamine, n-butylamine, isobutylamine, sec.-butylamine, tert.-butylamine, 2-propenylamine, 2-methylethenylamine, 2-butenylamine, 3-butenylamine, 1-methyl-2-propenylamine, 2-methyl-2-propenylamine, propargylamine, 2-butynylamine, 3-butynylamine and 1-methyl-2-propynylamine.

The 2,6-dihalopyrimidines XIV can be reacted with the amines XV in an aprotic polar solvent at from −80° to 40° C., either employing the amine XV in excess or using an additional organic base.

Examples of solvents suitable for the reaction of the 2,6-dihalopyrimidine XIV with the amine XV are the following:

Ethers such as methyl tert.-butyl ether, diethyl ether, ethyl propyl ether, n-butyl ethyl ether, di-n-butyl ether, diisobutyl ether, diisoamyl ether, diisopropyl ether, cyclohexyl methyl ether, tetrahydrofuran, 1 2-dimethoxyethane, diethylene glycol dimethyl ether and anisole, esters such as ethyl acetate, n-butyl acetate and isobutyl acetate, and chlorohydrocarbons such as methylene chloride, 1,1,2,2-tetrachloroethane, 1,1-dichloroethylene, 1,2-dichloroethane, chlorobenzene, 1,2-dichlorobenzene and 1-chloronaphthalene, and mixtures of these solvents.

The solvent is expediently used in an amount of from 100 to 2000% by weight, preferably 400 to 1200% by weight, based on the starting material XIV.

It is advantageous to add from 1.8 to 2.5, in particular 1.95 to 2.2, mole equivalents of the amine XV based on the starting material XIV over the course of 0.5 to 2 hours to the starting material XIV in one of the abovementioned solvents at from (−80°) to 40° C., preferably −70° to 25° C., to stir until the reaction is complete (after about 3 hours) and then to allow to warm to 25° C. for the working up.

If only approximately the stoichiometric amount of the amine XV is employed, it is expedient to add from 0.9 to 1.1 equivalents of an additional organic base based on starting material XIV. Suitable for this are the customary organic bases such as trimethylamine, triethylamine, ethyldiisopropylamine, triisopropylamine, N,N-dimethylaniline, N,N-dimethylcyclohexylamine, N-methylpyrrolidine, pyridine, quinoline, α-, β- or γ-picoline, 2,4- and 2,6-lutidine and triethylenediamine.

The reaction can be carried out under atmospheric or superatmospheric pressure, continuously or batchwise.

For the working up the reaction mixture is extracted with water to remove the salts, and the organic phase is dried and purified, e.g. by chromatography. However, it is also possible to concentrate the organic phase directly and to stir the residue with a solvent.

The 2-amino-4-fluoroalkoxypyrimidines of the formula IIIa according to the invention are advantageously obtained by reacting 2-amino-4-fluoroalkoxy-6-halopyrimidines of the formula IIIb

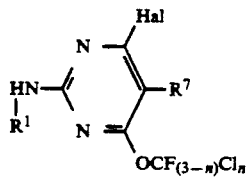

where Hal is fluorine, chlorine or bromine, and $R^1$ and n have the abovementioned meaning, with a nucleophile of the formula XVI

H-X-$R^2$    XVI where X and $R^2$ have the abovementioned meanings, or the salt thereof.

The reaction between 2-amino-4-fluoro-6-trifluoromethoxypyrimidine and methylamine is depicted in the following scheme:

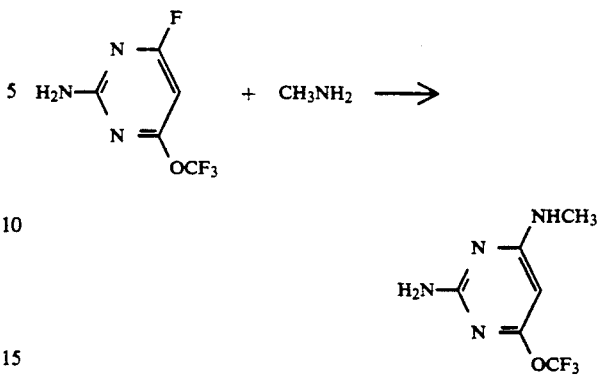

The reaction between 2-amino-4-fluoro-6-chlorodifluoromethoxypyrimidine and sodium methylate is depicted in the following scheme:

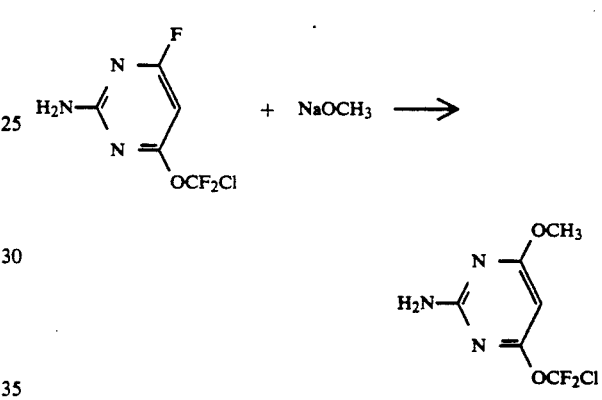

The process provides novel 2-amino-4-fluorolkoxypyrimidines in high yield and purity in a straight-forward and economic way. Unexpectedly, there is no substitution of fluoroalkoxy groups. The chlorine atom in the ether side chain is also retained despite the alkaline reaction conditions. In view of the prior art (see, for example, EP-A-70,804), all these advantageous properties are surprising.

Preferred intermediates IIIa and correspondingly preferred starting materials IIIb are those in whose formulae $R^1$ and $R^2$ are each $C_1$–$C_4$-alkyl such as methyl, ethyl, n-propyl, i-propyl, n-butyl, sec.-butyl, i-butyl or tert.-butyl, $C_3$–$C_4$-alkenyl such as 2-propenyl, 2-methylethenyl, 2-butenyl, 3-butenyl, 1-methyl-2-propenyl or 2-methyl-2-propenyl, or $C_3$–$C_4$-alkynyl such as propargyl, 2-butynyl, 3-butynyl or 1-methyl-2-propynyl, and $R^1$ can also be hydrogen.

X is O, S or N—$R^4$, where
$R^4$ is hydrogen, methyl, ethyl, n-propyl, i-propyl, n-butyl, sec.-butyl, i-butyl or tert.-butyl,
$R^7$ is hydrogen and
n is 0 or 1.

The reaction of the 2-amino-4-fluoroalkoxypyrimidine IIIb with a nucleophile XVI or salt thereof XVIa is carried out, for example, at from −80° to 80° C. Suitable nucleophiles XVI are ammonia, aliphatic amines, alcohols and thiols.

Among the amines which can be employed as nucleophiles, the following should be mentioned: ammonia, methylamine, ethylamine, n-propylamine, isopropylamine, n-butylamine, isobutylamine, sec.-butylamine, tert.-butylamine, 2-propenylamine, 2-methylethenylamine, 2-butenylamine, 3-butenylamine, 1-methyl-2-propenylamine, 2-methyl-2-propenylamine, propargylamine, 2-butynylamine, 3-butynylamine and 1-methyl-2-propynylamine, dimethylamine, diethylamine, di-n-propylamine, di-n-butylamine, N-methylethylamine, N-ethyl-n-propylamine, N-methylallylamine and N-methylpropargylamine.

Among the alcohols which can be employed as nucleophiles, the following should be mentioned: methanol, ethanol, n-propanol, i-propanol, n-butanol, i-butanol, sec.-butanol, tert.-butanol, 2-propenol, 2-methylethenol, 2-butenol, 3-butenol, 1-methyl-2-propenol, 2-methyl-2-propenol, propynol, 2-butynol, 3-butynol and 1-methyl-2-propynol.

Among the thiols which can be employed as nucleophiles, the following should be mentioned: methanethiol, ethanethiol, n-propanethiol, i-propanethiol, n-butanethiol, i-butanethiol, sec.-butanethiol, tert.-butanethiol, 2-methylethenethiol, 2-butenethiol, 3-butenethiol, 1-methyl-2-propenethiol, 2-methyl-2-propenethiol, propynthiol, 2-butynthiol, 3-butynthiol and 1-methyl-2-propynthiol.

The 4-halopyrimidines IIIb can be reacted with the amines XVI in an aprotic polar solvent at from $-80°$ to $+80°$ C., preferably $-30°$ to $+20°$ C., either employing the amine XVI in excess or using an additional organic base.

The following solvents are suitable for the reaction of the 4-halopyrimidine IIIb with the amine XVI:

Ethers such as methyl tert.-butyl ether, diethyl ether, ethyl propyl ether, n-butyl ethyl ether, di-n-butyl ether, diisobutyl ether, diisoamyl ether, diisopropyl ether, cyclohexyl methyl ether, tetrahydrofuran, 1,2-dimethoxyethane, diethylene glycol dimethyl ether and anisole, esters such as ethyl acetate, n-butyl acetate and isobutyl acetate, and chlorohydrocarbons such as methylene chloride, 1,1,2,2-tetrachloroethane, 1,1-dichloroethylene, 1,2-dichloroethane, chlorobenzene, 1,2-dichlorobenzene and 1-chloronaphthalene, and mixtures of these solvents.

The solvent is expediently used in an amount of from 100 to 2000% by weight, preferably 400 to 1200% by weight, based on the starting material IIIb.

It is advantageous to add from 1.8 to 2.5, in particular 1.95 to 2.2, mole equivalents of the amine XVI based on the starting material IIIb over the course of 0.5 to 2 hours to the starting material IIIb in one of the abovementioned solvents at from ($-80°$) to 80° C., preferably $-30°$ to 25° C., to stir until the reaction is complete (after about 3 hours) and then to allow to warm to 25° C. for the working up.

If only approximately stoichiometric amounts of the amine XVI is employed, it is expedient to add from 0.9 to 1.1 equivalents of an additional organic base based on starting material IIIb. Suitable for this are organic bases such as trimethylamine, triethylamine, ethyldiisopropylamine, triisopropylamine, N,N-dimethylaniline, N,N-dimethylcyclohexylamine, N-methylpyrrolidine, pyridine, quinoline, α-, β- or γ-picoline, 2,4- or 2,6-lutidine and triethylenediamine.

The reaction with alcohols or thiols can be carried out in a similar manner to that described for amines. The nucleophile is advantageously added in an amount of from 0.9 to 1.3 mole equivalents based on starting material IIIb over the course of from 0.5 to 2 hours together with one of the abovementioned bases to a mixture of starting material IIIb with one of the above-mentioned solvents at $-30°$ to 20° C., and the mixture is then stirred until the reaction is complete (about 3 hours) and then allowed to warm to 25° C. for the working up.

Besides the solvents mentioned, also suitable are ketones, e.g. acetone or methyl ethyl ketone, dipolar aprotic solvents, e.g. acetonitrile, dimethylformamide, dimethylacetamide, dimethyl sulfoxide, N-methylpyrrolidone and 1,3-dimethylimidazolin-2-one, aromatic compounds, e.g. benzene, toluene or xylene, or mixtures thereof. It is possible and advantageous when alcohols are employed as nucleophiles to use the latter directly as solvents. Salts of alcohols or thiols are particularly preferred and make the use of an additional organic base unnecessary. They are prepared in a conventional manner by use of alkali metals or alkaline earth metals or metal hydrides, e.g. NaH, KH, $CaH_2$ or LiH.

The reaction can be carried out under atmospheric or superatmospheric pressure, continuously or batchwise.

To work up the reaction mixture it is extracted with water to remove salts and is dried, and the organic phase is purified, e.g. by chromatography. However, in most cases the reaction products are sufficiently pure so that it is merely necessary to filter off the precipitated salt and to concentrate the organic phase.

Examples of preferred intermediates of the formula IIIa are:

2-amino-4-methoxy-6-trifluoromethoxypyrimidine,
2-amino-4-chlorodifluoromethoxy-6-methoxypyrimidine,
2-amino-4-ethoxy-6-trifluoromethoxypyrimidine,
2-amino-4-chlorodifluoromethoxy-6-ethoxypyrimidine,
2-amino-4-allyloxy-6-trifluoromethoxypyrimidine,
2-amino-4-allyloxy-6-chlorodifluoromethoxypyrimidine,
2-amino-4-methylthio-6-trifluoromethoxypyrimidine,
2-amino-4-chlorodifluoromethoxy-6-methylthiopyrimidine,
2-amino-4-ethylthio-6-trifluoromethoxypyrimidine,
2-amino-4-chlorodifluoromethoxy-6-ethylthiopyrimidine,
2-amino-4-methylamino-6-trifluoromethoxypyrimidine,
2-amino-4-chlorodifluoromethoxy-6-methylaminopyrimidine,
2-amino-4-ethylamino-6-trifluoromethoxypyrimidine,
2-amino-4-chlorodifluoromethoxy-6-ethylaminopyrimidine,
2-amino-4-dimethylamino-6-trifluoromethoxypyrimidine,
2-amino-4-chlorodifluoromethoxy-6-dimethylaminopyrimidine,
4-methoxy-2-methylamino-6-trifluoromethoxypyrimidine,
4-chlorodifluoromethoxy-6-methoxy-2-methylaminopyrimidine,
4-ethoxy-2-methylamino-6-trifluoromethoxypyrimidine,
4-chlorodifluoromethoxy-6-ethoxy-2-methylaminopyrimidine,
2,4-bis(methylamino)-6-trifluoromethoxypyrimidine,
4-chlorodifluoromethoxy-2,6-bis(methylamino)pyrimidine,
4-ethylamino-2-methylamino-6-trifluoromethoxypyrimidine,
4-chlorodifluoromethoxy-6-ethylamino-2-methylaminopyrimidine,
4-dimethylamino-2-methylamino-6-trifluoromethoxypyrimidine, 4-chlorodifluoromethoxy-6-dimethylamino-2-methylaminopyrimidine.

EMBODIMENT C

A sulfonamide of the formula V is reacted in a conventional manner (EP-A-141,777) in an inert organic solvent with approximately the stoichiometric amount of a phenyl carbamate VI at from 0° to 120° C., preferably 20° to 100° C. The reaction can be carried out under atmospheric or superatmospheric (up to 50 bar) pressure, preferably under from 1 to 5 bar, continuously or batchwise.

Suitable solvents are, besides those listed in the literature cited above, e.g. nitrohydrocarbons such as nitroethane and nitrobenzene, nitriles such as acetonitrile and benzonitrile, esters such as ethyl acetate, amides such as dimethylformamide and/or ketones such as acetone. The reaction is preferably carried out in ethyl acetate as solvent and with pyridine or one of the abovementioned tertiary amines as base.

The sulfonamides required as starting materials of the formula V can be prepared from substituted anilines, e.g. anthranilic esters or imides, 2-haloanilines or 2-haloalkylanilines by the Meerwein reaction and subsequent reaction with ammonia.

Compounds of the formula I where $R^5$ is hydrogen are obtained by hydrolysis of esters of the formula I where $R^5$ is $C_1$–$C_6$-alkyl. The hydrolysis is carried out with at least twice the amount of a base such as sodium or potassium hydroxide, expediently in a solvent mixture containing 2 to 8 times the amount of methanol and 10 to 40 times the amount of water based on the weight of the relevant ester of the formula I, at from 30° to 80° C. for from 1 to 20 hours. The sulfonamide carboxylic acids of the formula I are precipitated by acidification.

With a view to the biological activity, preferred compounds of the formula I have the following meanings for the substituents:

$R^1$ is hydrogen or methyl, $R^2$ is fluorine, chlorine, bromine or trifluoromethyl (m=0), and methyl, ethyl, n-propyl or isopropyl (m=1), $R^3$ is hydrogen, fluorine, chlorine, bromine, methyl, methoxy or trifluoromethyl, X is oxygen, sulfur or -$NR^4$ where $R^4$ is hydrogen, methyl or ethyl, A is chlorine, trifluoromethyl, carboxyl or carbamoyl, $R^5$ is $C_3$–$C_6$-alkyl such as methyl, ethyl, n-propyl or isopropyl, alkenyl such as allyl, crotyl or but-1-en-3-yl, alkynyl such as propargyl, but-1-yn-3-yl and but-2-ynyl, haloalkyl such as 2-chloroethyl, 2-chloro-n-propyl, 3-chloro-n-propyl, 1-chloro-2-butyl, 2-chloroisobutyl, 4-chloro-n-butyl, chloro-tert.-butyl, 3-chloro-2-propyl and 2,2,2-trifluoroethyl, alkoxyalkyl such as 2-methoxyethyl, 2-ethoxyethyl, 3-methoxy-n-propyl, 2-methoxy-n-propyl, 3-methoxy-n-butyl, 1-methoxy-2-butyl, methoxy-tert.-butyl, 2-methoxy-n-butyl and 4-methoxy-n-butyl, alkoxyalkoxyalkyl such as 2-methoxyethoxymethyl, 2-(ethoxy)ethoxymethyl, 2-(propoxy)ethoxymethyl, 2-methoxyethoxyethyl, 2-(ethoxy)ethoxyethyl and 2-(methoxymethoxy)ethyl, haloalkoxyalkyl such as 2-($\beta$-chloroethoxy)ethyl, 3-($\beta$-chloroethoxy)-n-propyl and 3-($\gamma$-chloro-n-propoxy)-n-propyl, cycloalkyl such as cyclopentyl and cyclohexyl, $R^6$ is hydrogen, alkyl such as methyl, ethyl, n-propyl, isopropyl and n-butyl, or together with $R^5$ is tetramethylene, pentamethylene, hexamethylene, ethyleneoxyethylene and ethylene-N-methyliminoethylene, $R^7$ is hydrogen and n is 0 or 1.

Suitable salts of the compounds of the formula I are salts which can be used in agriculture, for example alkali metal salts such as the potassium or sodium salt, alkaline earth metal salts such as the calcium, magnesium or barium salt, manganese, copper, zinc or iron salts, and ammonium, phosphonium, sulfonium or sulfoxonium salts, for example ammonium salts, tetraalkylammonium salts, benzyltrialkylammonium salts, trialkylsulfonium salts or trialkylsulfoxonium salts.

The herbicidal and growth-regulating compounds I, or agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90%, by weight of active ingredient. The active ingredients are employed in a purity of from 90 to 100, and preferably from 95 to 100%, (according to the NMR spectrum).

The compounds I according to the invention may be formulated for instance as follows:

I. 90 parts by weight of compound no. 1.001 is mixed with 10 parts by weight of N-methyl-alpha-pyrrolidone. A mixture is obtained which is suitable for application in the form of very fine drops.

II. 20 parts by weight of compound no. 1.003 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 2.001 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 3.001 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 5.001 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 6.001 is intimately mixed with 97 parts by weight of particulate kaolin. A dust is obtained containing 3% by weight of the active ingredient.

VII. 30 parts by weight of compound no. 7.001 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 1.001 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal and growth-regulating agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

When the active ingredients are used as herbicides, the application rates depend on the objective to be achieved, the time of the year, the plants to be combated and their growth stage, and are from 0.001 to 2, preferably 0.01 to 1, kg of active ingredient per hectare.

The compounds of the formula I may exercise a variety of influences on practically all plant development stages, and are therefore used as growth regulators. The diversity of action of growth regulators depends especially on a) the type and variety of plant;
b) the time applied, with reference to the development stage of the plants and the time of the year;
c) the place and method of application (seed treatment, soil treatment, application to foliage, or trunk injection in the case of trees);
d) climatic factors, e.g., average temperature, amount of precipitate, sunshine and duration;
e) soil conditions (including fertilization);
f) the formulation of the active ingredient; and
g) the concentration at which the active ingredient is applied.

A description of some of the various possibilities of using the growth regulators according to the invention in agriculture and horticulture is given below.

A. vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, hedges, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

In fruit and other trees, pruning costs can be reduced with growth regulators. With growth regulators, it is also possible to break up the alternate breeding rhythm of fruit trees.

Growth regulators may also increase or inhibit lateral branching. This is of interest when, for instance in tobacco plants, it is desired to inhibit the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases. The inhibition of vegetative growth also makes closer planting possible in numerous crops, which means an increase in yield, based on the area cropped.

B. Better yields both of plant parts and plant materials may be obtained with the novel agents. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The compounds of the formula I may raise the yield by influencing plant metabolism or by promoting or inhibiting vegetative and/or generative plant growth.

C. It is also possible with growth regulators to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants, e.g., cotton.

D. Further, transpiration in crop plants may be reduced with growth regulators. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized, because, inter alia, the size of the stomata opening is reduced;

a thicker epidermis and cuticle are formed;
penetration of the soil by the roots is improved;
the micro-climate in the stand is favorably influenced by the more compact growth.

The growth regulators to be used according to the invention may be applied not only to the seed (as a disinfectant), but also to the soil, i.e., via the roots, and—the method particularly preferred—to the foliage by spraying.

As a result of the good tolerance by crop plants, the application rate may vary within wide limits.

In view of the numerous application methods possible, the compounds according to the invention, or agents containing them, may be used in a large number of crops. Those which follow are given by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sative | oats |
| Beta vulgaris spp. altissima | sugarbeets |
| Beta vulgaris spp. rapa | fodder beets |
| Brassica napus var. napus | rapeseed |
| Brassica npaus var. napobrassica | swedes |
| Brassica rapa var. silvestris | |
| Camellia sinesis | tea plants |
| Carthamus tinctorius | safflower |
| Carya illinoinensis | pecan trees |
| Citrus limon | lemons |
| Citrus sinensis | orange trees |
| Coffea arabica (Coffea canephore, Coffea liberica) | coffee plants |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |
| Malus spp. | apple trees |
| Manihot esculaenta | cassava |
| Medicago sativa | alfalfa (lucerne) |
| Musa spp. | banana plants |
| Nicotiana tabacum (N. rustica) | tobacco |
| Olea europaea | olive trees |
| Oryza sative | rice |
| Phaseolus lunatis | limabeans |
| Phaseolus vulgaris | snapbeans, green beans, dry beans |
| Picea abies | Norway spruce |
| Pinus spp. | pine trees |
| Pisum sativum | English peas |
| Prunus avium | cherry trees |
| Prunus persica | peach trees |
| Pyrus communis | pear trees |
| Ribes sylvestre | redcurrants |
| Rincinus communis | castor-oil plants |
| Saccharum officinarum | sugar cane |
| Secale cereale | rye |
| Solanum tuberosum | Irish potatoes |
| Sorghum bicolor (s. vulgare) | sorghum |
| Theobroma cacoa | cacoa plants |
| Trifolium pratense | red clover |
| Triticum aestivum | wheat |
| Triticum durum | durum wheat |
| Vicia faba | tick beans |

| Botanical name | Common name |
|---|---|
| *Vitis vinifera* | grapes |
| *Zea mays* | Indian corn, sweet corn, maize |

To increase the spectrum of action and to achieve synergistic effects, the compounds I according to the invention may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acid derivatives, aryloxy- and heteroaryloxyphenoxypropionic acids and their salts, esters and amides, etc.

It may also be useful to apply the novel compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS EXAMPLES

The directions given in the synthesis examples below were used, after appropriate modifications of the starting materials, to produce further compounds of the formula I. The compounds obtained are given in the following tables with their physical data. Compounds without these data may be produced analogously from the appropriate materials. In view of their close structural relationship with the compounds which have been produced and investigated, they can be expected to have a similar action.

I MANUFACTURE OF THE PRECURSORS

Example I.1

2-Chloro-4-trichloromethoxy-6-trichloromethylpyrimidine a) 2-Chloro-4-methoxy-6-trichloromethylpyrimidine While stirring and within a period of 1 ½ hours at 0° to 5° C., 293.1 g (1.692 mol) of a 30% strength sodium methylate solution was added to a solution of 434 g (1.692 mol) of 2,6-dichloro-4-trichloromethylpyrimidine in 1 liter of 1,2-dichloroethane. The mixture was stirred for 1 hour at 0° to 5° C. and for 12 hours at 25° C. The reaction mixture was then extracted with water and saturated sodium chloride solution. After drying over magnesium sulfate and evaporating down, there was obtained 423 g (95% of theory) of the title compound as an almost colorless oil of $n_D^{23}=1.5552$. $^1$H-NMR (CDCl$_3$) (ppm) OCH$_3$ (s/3H) 4.1; CH (s/1H) 7.25.

b) 2-Chloro-4-trichloromethoxy-6-trichloromethylpyrimidine

At initially 110° C., chlorine was introduced, with infrared irradiation and gas-chromatographic monitoring of the course of the reaction, into a mixture of 210 g (0.802 mol) of a) and 260 mg (0.0016 mol) of $\alpha,\alpha'$-azoisobutyronitrile; the reaction temperature reached 140° C., even after removal of the heating bath. After the reaction had subsided, a total of 341 g (4.8 mol) of chlorine was introduced over a period of 5 ½ hours at 120° C. To aid precipitation, 70 ml of n-pentane was stirred into the cooling reaction mixture from 40° C. The precipitate was suction filtered, washed with ligroin and dried. There was obtained 163 g (55% of theory) of the title compound; m.p. 67°-69° C.

The filtrate (113.8 g) consisted, according to the gas chromatograph, of 83% of the title compound, 4% of 2-chloro-4-dichoromethoxy-6-trichloromethylpyrimidine and 9% of 2,4-dichloro-6-trichloromethylpyrimidine. The total yield of the title compound was 87.6% of theory.

Example I.2

2,4-Difluoro-6-trichloromethoxypyrimidine a) 2,4-Difluoro-6-methoxypyrimidine (According to the process of prior German Patent Application P 39 00 471 (O.Z. 0050/40474)).

At $-20°$ C. and over a period of 45 minutes, 335.8 g (1.865 mol) of 30% strength sodium methylate (in methanol) was added to a mixture of 250 g (1.865 mol) of 2,4,6-trifluoropyrimidine, and the mixture was stirred for a further 30 minutes at this temperature. The temperature was then allowed to rise to 25° C., and the reaction mixture was evaporated down to about one fifth of its volume.

The mixture obtained was partitioned between diethyl ether and water, after which the organic phase was dried over magnesium sulfate and evaporated down. Distillation (1.1 meter column, 3 mm V-shaped packings) gave 141.6 g (52% of theory) of the title compound of boiling point 144°-145° C.

Distillation of the residue through a fractionating column (from Normag) gave 114.4 g (42% of theory) of 4,6-difluoro-2-methoxypyrimidine of boiling point 157°-161° C.

b) 2,4-Difluoro-6-trichloromethoxypyrimidine

With UV irradiation and gas-chromatographic monitoring of the course of the reaction, 210 g (2.96 mol) of chlorine was introduced over a period of 2 ½ hours and with stirring at 130° C. into 123 g (0.843 mol) of 2,4-difluoro-6-methoxypyrimidine. The reaction mixture was distilled through a 10 cm vigreux column under reduced pressure, 190.2 g (90.5% of theory) of the title compound of boiling point 40°-43° C./0.2 mbar being obtained.

Example I.3

2,4-Dichloro-6-trichloromethoxypyrimidine

With stirring, UV irradiation and gas-chromatographic monitoring of the course of the reaction, 303 g (4.27 mol) of chlorine was passed over a period of 30 minutes at 80° C., 1 hour at 100° C., 3 hours at 120° C. and 3 hours at 150° C. into a mixture of 209 g (1.168 mol) of 2,6-dichloro-4-methoxypyrimidine and 2 g (0.012 mol) of $\alpha,\alpha'$-azoisobutyronitrile. The reaction mixture was then distilled under reduced pressure through a 50 cm column containing V2-A Raschig rings. There was obtained 241.3 g (73% of theory) of the title compound of boiling point 87°-88° C./0.4 mbar; melting point 55°-56° C.

Example I.4

2,4-Difluoro-6-trifluoromethoxypyrimidine

At 100° C. and over a period of 15 minutes, 49.9 g (0.2 mol) of 2,4-difluoro-6-trichloromethoxypyrimidine was added, with stirring, to a mixture of 39.3 g (0.22 mol) of antimony trifluoride and 9.38 g (0.031 mol) of antimony pentachoride.

The bath temperature was raised over a period of 25 minutes from 100° to 150° C. and the mixture was stirred for 30 minutes at this temperature, reflux being set up between 120° and 125° C. Subsequent distillation gave 37.1 g (92.7% of theory) of the title compound of boiling point 125°–127° C. and $n_D^{23}=1.3787$.

Example I.5

6-Chlorodifluoromethoxy-2,4-difluoropyrimidine

At 100° C. and over a period of 10 minutes, 93 g (0.373 mol) of 2,4-difluoro-6-trichloromethoxypyrimidine was added with stirring to a mixture of 44.5 g (0.249 mol) of antimony trifluoride and 0.94 g (0.0031 mol) of antimony pentachloride. The bath temperature was raised over a period of 25 minutes from 100° to 175° C., reflux being set up at 145° C. After the mixture had been stirred for 1 ½ hours, the reaction product was distilled off at 146°–150° C. The distillate was dissolved in 200 ml of methylene chloride, extracted twice with 6N hydrochloric acid and dried over magnesium sulfate. Evaporation under reduced pressure gave as residue the title compound of $n_D^{23}=1.4142$ in a yield of 63.7 g (78.8% of theory).

Example I.6

2-Fluoro-4-trifluoromethoxy-6-trifluoromethylpyrimidine

At 100° C. and over a period of 5 minutes, 80 g (0.219 mol) of 2-chloro-4-trichloromethyl-6-trichloromethoxypyrimidine was added with stirring to a mixture of 93.9 g (0.525 mol) of antimony trifluoride and 18.7 g (0.0627 mol) of antimony pentachloride. The bath temperature was raised over a period of 10 minutes to 140° C., and then stirred for 1 hour, strong reflux being set up. The reaction product distilled over at 135°–140° C., and toward the end at 95° C./50 mbar. The distillate was taken up in methylene chloride, extracted with 6N hydrochloric acid and dried over magnesium sulfate. Evaporation under reduced pressure gave the title compound in a yield of 35.9 g (65.5% of theory).

Example I.7

2,4-Dichloro-6-trifluoromethoxypyrimidine

At 100° C. and over a period of 5 minutes, 115 g (0.407 mol) of 2,4-dichloro-6-trichloromethoxypyrimidine was added while stirring to a mixture of 80 g (0.477 mol) of antimony trifluoride and 18.77 g (0.0627 mol) of antimony pentachloride, the temperature of the reaction mixture increasing to 140° C. The mixture was stirred for a further 45 minutes at 150° C. For distillation, a pressure of 210 mbar was set up, the title compound passing over at 128° C.; the last volatile constituents passed over at 110° C./22 mbar. The distillate was dissolved in methylene chloride, extracted three times with 6N hydrochloric acid and dried over magnesium sulfate. Evaporation under reduced pressure gave the title compound in a yield of 80 g (84.4% of theory) as a colorless oil of $n_D^{25}=1.4604$.

Example I.8

2-Amino-4-chlorodifluoromethoxy-6-fluoropyrimidine

At −75° to −70° C. and over a period of 1 hour, 9.8 g (0.578 mol) of gaseous ammonia was gassed while stirring into a mixture of 62.5 g (0.289 mol) of 2,4-difluoro-6-chlorodifluoromethoxypyrimidine in 300 ml of tetrahydrofuran. The mixture was stirred for 1 hour at −70° C. and then heated to room temperature. The precipitate was suction filtered, partitioned between ethyl acetate and water, and the organic phase was dried over magnesium sulfate. The reaction filtrate was evaporated down, dissolved in the abovementioned ethyl acetate phase, chromatographed over silica gel (5:1 ligroin/ether mixture) and evaporated down. There was obtained 46.5 g (75.3% of theory) of the title compound as colorless crystals of melting point 77°–80° C.

Example I.9

2-Amino-4-fluoro-6-trifluoromethoxypyrimidine

At −75° to −70° C. and over a period of 1 hour, 8.7 g (0.51 mol) of gaseous ammonia was gassed, while stirring, into a mixture of 51 g (0.255 mol) of 2,4-difluoro-6-trifluoromethoxypyrimidine in 200 ml of diethyl ether. The mixture was stirred for 1 ½ hours at −70° C. and for 1 hour at room temperature. The reaction mixture was evaporated down under reduced pressure, taken up in methylene chloride and extracted with water. The organic phase was dried, evaporated down and chromatographed over silica gel (8:1 ligroin/ether mixture) to give 38.1 g (75.6% of theory) of the title compound as colorless crystals of melting point 86°–89° C.

Example I.10

2-Amino-4-chloro-6-trifluoromethoxypyrimidine

At −50° to −45° C. and over a period of 45 minutes, 4.3 g (0.25 mol) of gaseous ammonia was passed, while stirring, into a mixture of 23.3 g (0.1 mol) of 2,4-dichloro-6-trifluoromethoxypyrimidine in 150 ml of methyl tert-butyl ether. The mixture was stirred for 30 minutes at −50° C., 1 hour at −30° C. and for 1 hour at 25° C. The precipitate was suction filtered, washed with water and dried, giving 5.4 g (33.1% of theory) of 4-amino-2,4-dichloropyrimidine of melting point 270°–272° C. as byproduct. The filtrate was washed with water, dried, evaporated down partially under reduced pressure, and fractionally chromatographed with a 5:1 ligroin/ether mixture, the first fractions giving 3 g (12.81% of theory) of the starting material as a colorless oil and the last runnings 9 g (42% of theory) of the title compound as colorless crystals of melting point 55°–56° C. The conversion was 48.3%.

Example I.11

4-Chlorodifluoromethoxy-6-fluoro-2-methylaminopyrimidine

At −70° to −60° C. and over a period of 30 minutes, 5.8 g (0.188 mol) of gaseous methylamine was added, with stirring, to 20.3 g (0.0938 mol) of 4-chlorodifluoromethoxy-2,6-difluoropyrimidine in 150 ml of tetrahydrofuran. The mixture was stirred for 1 hour at −70° C., 1 hour at 0° C. and 1 hour at 25° C., and then evaporated down under reduced pressure. The residue was stirred with water and extracted twice with ethyl acetate, and the extract was dried over magnesium sulfate. It was evaporated down, partially under reduced pressure, and then fractionally chromatographed over silica gel (1:5 ether/ligroin mixture). The first fractions contained the title compound (melting point 57°-61° C.) in a yield of 12.5 g (58.5%).

Example 1.12

2-Amino-4-trifluoromethoxy-6-trifluoromethylpyrimidine

At −75° to −70° C. and over a period of 1 hour, 4.7 g (0.278 mol) of gaseous ammonia was gassed, while stirring, into a mixture of 38.0 g (0.147 mol) of 2-fluoro(-chloro)-4-trifluoromethoxy-6-trifluoromethylpyrimidine in 150 ml of diethyl ether. The mixture was stirred for 2 hours at −75° C. and for 2 hours at 25° C. The precipitate was suction filtered, and the organic phase was extracted with water, dried and partially evaporated down. Chromatography with methyl tert-butyl ether over silica gel gave 20.4 g (56.1% of theory) of the title compound of melting point 47°-49° C.

II. Manufacture of the intermediates IIIa

Example II.1

2-Amino-4-methoxy-6-trifluoromethoxypyrimidine

At −5° to 0° C. and over a period of 15 minutes, 2.7 g (0.015 mol) of 30% strength sodium methylate was added, while stirring, to 2.95 g (0.015 mol) of 2-amino-4-fluoro-6-trifluoromethoxypyrimidine in 50 ml of methanol. The reaction mixture was stirred for 1 hour at 0° C., heated to 25° C., evaporated down under reduced pressure, stirred with water and extracted twice with methylene chloride. Drying and evaporation under reduced pressure gave 3.1 g (98% of theory) of the title compound; $n_D^{25} = 1.4770$.

Example II.2

2-Amino-4-chlorodifluoromethoxy-6-methoxypyrimidine

At −10° to 0° C. and over a period of 15 minutes, 26.1 g (0.145 mol) of 30% strength sodium methylate was added, while stirring, to 31.0 g (0.145 mol) of 2-amino-4-chlorodifluoromethoxy-6-fluoropyrimidine in 300 ml of methanol. The mixture was stirred for 30 minutes at 0° C. and for 1 hour at 25° C. The reaction mixture was evaporated down under reduced pressure and worked up as above. There was obtained 31.6 g (96.6% of theory) of the title compound as a colorless oil; $n_D^{22} = 1.5039$.

Example II.3

4-Chlorodifluoromethoxy-2-methylamino-6-methoxypyrimidine

At 0° C. and over a period of 10 minutes, 4.7 g (0.026 mol) of 30% strength sodium methylate was added, while stirring, to 6.0 g (0.0263 mol) of 4-chlorodifluoromethoxy-6-fluoro-2-methylaminopyrimidine in 100 ml of methanol. The mixture was stirred for 1 hour at 0° C. and for 1 hour at 25° C. Conventional working up gave 6.3 g (100% of theory) of the title compound of melting point 49°-53° C.

Example II.4

4-Chlorodifluoromethoxy-6-dimethylamino-2-methylaminopyrimidine

At 0° C. and over a period of 10 minutes, 1.9 g (0.0417 mol) of gaseous dimethylamine was added, while stirring, to a mixture of 8.9 g (0.0417 mol) of 2-amino-4-chlorodifluoromethoxy-6-fluoropyrimidine in 100 ml of tetrahydrofuran. The mixture was stirred for 1 hour at 0° C. and for 2 hours at 25° C. Conventional working up gave 9.7 g (97.5% of theory) of the title compound of melting point 127°-130° C.

III. MANUFACTURE OF THE SULFONYLUREA COMPOUNDS I

Example III.1

Methyl 2-(((4-fluoro-6-trifluoromethoxy-1,3-pyrimidin-2-yl)-aminocarbonyl)-aminosulfonyl)-benzoate At 25° C. and over a period of 15 minutes, 3.6 g (0.015 mol) of methyl 2-isocyanatosulfonyl benzoate in 15 ml of 1,2-dichloroethane was introduced, while stirring, into a mixture of 2.95 g (0.015 mol) of 2-amino-4-fluoro-6-trifluoromethoxypyrimidine in 100 ml of 1,2-dichloroethane, and the whole was stirred for 12 hours at 25° C. The reaction solution was evaporated down under reduced pressure and the residue was stirred with ether/ligroin (1:1). Suction filtration and drying gave 4.8 g (73.3% of theory) of the title compound of melting point 157°-161° C.

(Active ingredient example no. 1.001)

Example III.2

Ethyl 2-(((4-chloro-6-trifluoromethoxy-1,3-pyrimidin-2-yl)-aminocarbonyl)aminosulfonyl)-benzoate At 25° C. and over a period of 10 minutes, 2,55 g (0.01 mol) of ethyl 2-isocyanatosulfonylbenzoate in 10 ml of methylene chloride was added, while stirring, to a mixture of 2.1 g (0.01 mol) of 2-amino-4-chloro-6-trifluoromethoxypyrimidine in 100 ml of methylene chloride. The mixture was stirred for 12 hours at 25° C. and separated from a small amount of insoluble matter by suction filtration. The filtrate was evaporated down under reduced pressure, and the residue was stirred with ether/ligroin (1:1), suction filtered and dried. There was obtained 4.0 g (85.4% of theory) of the title compound of melting point 148°-151° C.

(Active ingredient example no. 3.003)

Example III.3

Methyl 2-(((4-methoxy-6-trifluoromethoxy-1,3-pyrimidin-2-yl)-aminocarbonyl)-aminosulfonyl)-benzoate At 25° C. and over a period of 15 minutes, 4.8 g (0.02 mol) of methyl 2-isocyanatosulfonylbenzoate in 10 ml of acetonitrile was added, while stirring, to a mixture of 4.1 g (0.02 mol) of 2-amino-4-methoxy-6-trifluoromethoxypyrimidine in 100 ml of acetonitrile, and the whole was stirred for 12 hours. The precipitate was separated off (2.4 g of melting point 141°-143° C.) and the filtrate was evaporated down under reduced pressure, stirred with ether/ligroin, suction filtered and dried. A further 4.3 g of the title compound of melting point 141°-143° C. was obtained. The total yield was 6.7 g (74.4% of theory).

(Active ingredient example no. 5.001)

Example III.4

Methyl 2-(((4-methoxy-6-trifluoromethoxy-1,3-pyrimidin-2-yl)-aminocarbonyl)-aminosulfonyl)-benzoate, sodium salt 2.4 g (0.053 mol) of methyl 2-(((4-methoxy-6-trifluoromethoxy-1,3-pyrimidin-2-yl)-aminocarbonyl)-aminosulfonyl)-benzoate (active ingredient example 5.001) was dissolved in 50 ml of methanol. At 25° C., 1.0 g (0.053 mol) of 30% strength sodium methylate solution in methanol was added and the mixture stirred for 10 minutes. After the solvent had been distilled off under reduced pressure, there was obtained 2.5 g (100% of theory) of the title compound of melting point 175° C. (decomposition).

(Active ingredient example no. 5.019)

The sulfonylurea derivatives given in the tables which follow were prepared analogously.

TABLE 1

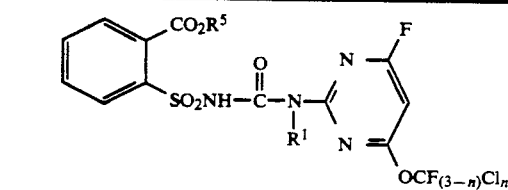

| No. | $R^1$ | $R^5$ | n | mp (°C.) | |
|---|---|---|---|---|---|
| 1.001 | H | $CH_3$ | 0 | 157–161 | |
| 1.002 | $CH_3$ | $CH_3$ | 0 | | |
| 1.003 | H | $CH_2CH_3$ | 0 | 148–150 | |
| 1.004 | $CH_3$ | $CH_2CH_3$ | 0 | | |
| 1.005 | H | $(CH_2)_2CH_3$ | 0 | | |
| 1.006 | $CH_3$ | $(CH_2)_2CH_3$ | 0 | | |
| 1.007 | H | $CH(CH_3)_2$ | 0 | 164–168 | |
| 1.008 | H | $CH_2-CH=CH_2$ | 0 | | |
| 1.009 | H | $CH_2-CH=CH-CH_3$ | 0 | | |
| 1.010 | H | $CH_2-C\equiv C-CH_3$ | 0 | | |
| 1.011 | H | $(CH_2)_2Cl$ | 0 | | |
| 1.012 | $CH_3$ | $(CH_2)_2Cl$ | 0 | | |
| 1.013 | H | $(CH_2)_2OCH_3$ | 0 | | |
| 1.014 | H | $(CH_2)_2O(CH_2)_2OCH_3$ | 0 | | |
| 1.015 | H | Cyclopentyl | 0 | | |
| 1.016 | H | Cyclohexyl | 0 | | |
| 1.017 | H | $CH_2CF_3$ | 0 | | |
| 1.018 | H | $(CH_2)_2SCH_3$ | 0 | | |
| 1.019 | H | $CH_3$ | 0 | 113 decomp. | Na salt |
| 1.020 | $CH_3$ | $CH_3$ | 0 | | Na salt |
| 1.021 | H | $CH_2CH_3$ | 0 | 130 decomp. | Na salt |
| 1.022 | $CH_3$ | $CH_2CH_3$ | 0 | | Na salt |
| 1.023 | H | $(CH_2)_2CH_3$ | 0 | | Na salt |
| 1.024 | H | $(CH_2)_2Cl$ | 0 | | Na salt |
| 1.025 | H | $CH(CH_3)_2$ | 0 | 140–145 decomp. | Na salt |
| 1.026 | H | $C_2H_5$ | 0 | 135 decomp. | Ca salt |

TABLE 2

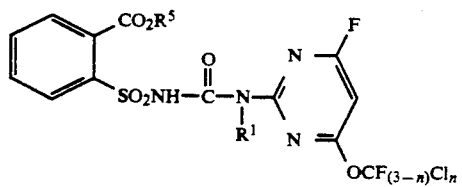

| No. | $R^1$ | $R^5$ | n | mp (°C.) |
|---|---|---|---|---|
| 2.001 | H | $CH_3$ | 1 | 167–170 |
| 2.002 | $CH_3$ | $CH_3$ | 1 | |
| 2.003 | H | $CH_2CH_3$ | 1 | |
| 2.004 | $CH_3$ | $CH_2CH_3$ | 1 | |
| 2.005 | H | $(CH_2)_2CH_3$ | 1 | |
| 2.006 | $CH_3$ | $(CH_2)_2CH_3$ | 1 | |

TABLE 2-continued

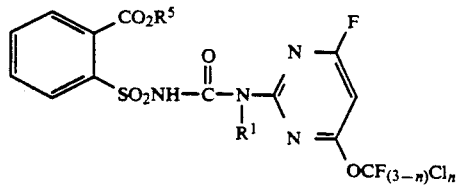

| No. | $R^1$ | $R^5$ | n | mp (°C.) | |
|---|---|---|---|---|---|
| 2.007 | H | $CH(CH_3)_2$ | 1 | | |
| 2.008 | H | $CH_2-CH=CH_2$ | 1 | | |
| 2.009 | H | $CH_2-CH=CH-CH_3$ | 1 | | |
| 2.010 | H | $CH_2-C\equiv C-CH_3$ | 1 | | |
| 2.011 | H | $(CH_2)_2Cl$ | 1 | | |
| 2.012 | $CH_3$ | $(CH_2)_2Cl$ | 1 | | |
| 2.013 | H | $(CH_2)_2OCH_3$ | 1 | | |
| 2.014 | H | $(CH_2)_2O(CH_2)_2OCH_3$ | 1 | | |
| 2.015 | H | Cyclopentyl | 1 | | |
| 2.016 | H | Cyclohexyl | 1 | | |
| 2.017 | H | $CH_2CF_3$ | 1 | | |
| 2.018 | H | $(CH_2)_2SCH_3$ | 1 | | |
| 2.019 | H | $CH_3$ | 1 | 195 decomp. | Na salt |
| 2.020 | $CH_3$ | $CH_3$ | 1 | | Na salt |
| 2.021 | H | $CH_2CH_3$ | 1 | | Na salt |
| 2.022 | $CH_3$ | $CH_2CH_3$ | 1 | | Na salt |
| 2.023 | H | $(CH_2)_2CH_3$ | 1 | | Na salt |
| 2.024 | H | $(CH_2)_2Cl$ | 1 | | Na salt |

TABLE 3

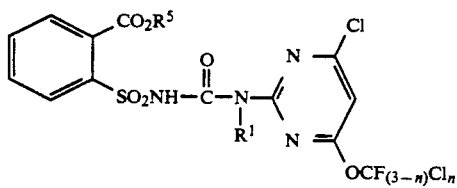

| No. | $R^1$ | $R^5$ | n | mp (°C.) | |
|---|---|---|---|---|---|
| 3.001 | H | $CH_3$ | 0 | 186–187 | |
| 3.002 | $CH_3$ | $CH_3$ | 0 | | |
| 3.003 | H | $CH_2CH_3$ | 0 | 148–151 | |
| 3.004 | $CH_3$ | $CH_2CH_3$ | 0 | | |
| 3.005 | H | $(CH_2)_2CH_3$ | 0 | | |
| 3.006 | $CH_3$ | $(CH_2)_2CH_3$ | 0 | | |
| 3.007 | H | $CH(CH_3)_2$ | 0 | | |
| 3.008 | H | $CH_2-CH=CH_2$ | 0 | | |
| 3.009 | H | $CH_2-CH=CH-CH_3$ | 0 | | |
| 3.010 | H | $CH_2-C\equiv C-CH_3$ | 0 | | |
| 3.011 | H | $(CH_2)_2Cl$ | 0 | | |
| 3.012 | $CH_3$ | $(CH_2)_2Cl$ | 0 | | |
| 3.013 | H | $(CH_2)_2OCH_3$ | 0 | | |
| 3.014 | H | $(CH_2)_2O(CH_2)_2OCH_3$ | 0 | | |
| 3.015 | H | Cyclopentyl | 0 | | |
| 3.016 | H | Cyclohexyl | 0 | | |
| 3.017 | H | $CH_2CF_3$ | 0 | | |
| 3.018 | H | $(CH_2)_2SCH_3$ | 0 | | |
| 3.019 | H | $CH_3$ | 0 | 188 decomp. | Na salt |
| 3.020 | $CH_3$ | $CH_3$ | 0 | | Na salt |
| 3.021 | H | $CH_2CH_3$ | 0 | | Na salt |
| 3.022 | $CH_3$ | $CH_2CH_3$ | 0 | | Na salt |
| 3.023 | H | $(CH_2)_2CH_3$ | 0 | | Na salt |
| 3.024 | H | $(CH_2)_2Cl$ | 0 | | Na salt |

TABLE 4

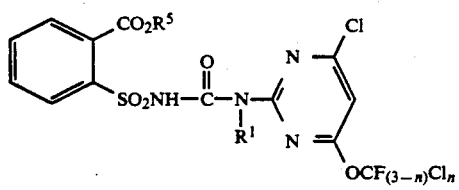

| No. | R¹ | R⁵ | n | mp (°C.) | |
|---|---|---|---|---|---|
| 4.001 | H | $CH_3$ | 1 | | |
| 4.002 | $CH_3$ | $CH_3$ | 1 | | |
| 4.003 | H | $CH_2CH_3$ | 1 | | |
| 4.004 | $CH_3$ | $CH_2CH_3$ | 1 | | |
| 4.005 | H | $(CH_2)_2CH_3$ | 1 | | |
| 4.006 | $CH_3$ | $(CH_2)_2CH_3$ | 1 | | |
| 4.007 | H | $CH(CH_3)_2$ | 1 | | |
| 4.008 | H | $CH_2-CH=CH_2$ | 1 | | |
| 4.009 | H | $CH_2-CH=CH-CH_3$ | 1 | | |
| 4.010 | H | $CH_2-C\equiv C-CH_3$ | 1 | | |
| 4.011 | H | $(CH_2)_2Cl$ | 1 | | |
| 4.012 | $CH_3$ | $(CH_2)_2Cl$ | 1 | | |
| 4.013 | H | $(CH_2)_2OCH_3$ | 1 | | |
| 4.014 | H | $(CH_2)_2O(CH_2)_2OCH_3$ | 1 | | |
| 4.015 | H | Cyclopentyl | 1 | | |
| 4.016 | H | Cyclohexyl | 1 | | |
| 4.017 | H | $CH_2CF_3$ | 1 | | |
| 4.018 | H | $(CH_2)_2SCH_3$ | 1 | | |
| 4.019 | H | $CH_3$ | 1 | | Na salt |
| 4.020 | $CH_3$ | $CH_3$ | 1 | | Na salt |
| 4.021 | H | $CH_2CH_3$ | 1 | | Na salt |
| 4.022 | $CH_3$ | $CH_2CH_3$ | 1 | | Na salt |
| 4.023 | H | $(CH_2)_2CH_3$ | 1 | | Na salt |
| 4.024 | H | $(CH_2)_2Cl$ | 1 | | Na salt |

TABLE 6

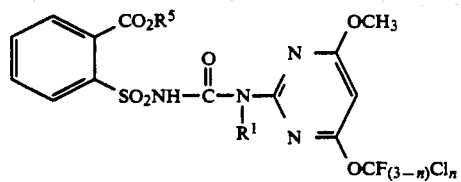

| No. | R¹ | R⁵ | n | mp (°C.) | |
|---|---|---|---|---|---|
| 6.001 | H | $CH_3$ | 1 | 124-127 | |
| 6.002 | $CH_3$ | $CH_3$ | 1 | 79-83 | |
| 6.003 | H | $CH_2CH_3$ | 1 | 133-136 | |
| 6.004 | $CH_3$ | $CH_2CH_3$ | 1 | | |
| 6.005 | H | $(CH_2)_2CH_3$ | 1 | | |
| 6.006 | $CH_3$ | $(CH_2)_2CH_3$ | 1 | | |
| 6.007 | H | $CH(CH_3)_2$ | 1 | | |
| 6.008 | H | $CH_2-CH=CH_2$ | 1 | | |
| 6.009 | H | $CH_2-CH=CH-CH_3$ | 1 | | |
| 6.010 | H | $CH_2-C\equiv C-CH_3$ | 1 | | |
| 6.011 | H | $(CH_2)_2Cl$ | 1 | | |
| 6.012 | $CH_3$ | $(CH_2)_2Cl$ | 1 | | |
| 6.013 | H | $(CH_2)_2OCH_3$ | 1 | | |
| 6.014 | H | $(CH_2)_2O(CH_2)_2OCH_3$ | 1 | | |
| 6.015 | H | Cyclopentyl | 1 | | |
| 6.016 | H | Cyclohexyl | 1 | | |
| 6.017 | H | $CH_2CF_3$ | 1 | | |
| 6.018 | H | $(CH_2)_2SCH_3$ | 1 | | |
| 6.019 | H | $CH_3$ | 1 | 148 decomp. | Na salt |
| 6.020 | $CH_3$ | $CH_3$ | 1 | | Na salt |
| 6.021 | H | $CH_2CH_3$ | 1 | | Na salt |
| 6.022 | $CH_3$ | $CH_2CH_3$ | 1 | | Na salt |
| 6.023 | H | $(CH_2)_2CH_3$ | 1 | | Na salt |
| 6.024 | H | $(CH_2)_2Cl$ | 1 | | Na salt |

TABLE 5

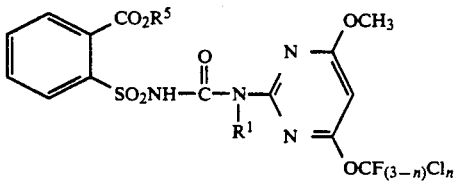

| No. | R¹ | R⁵ | n | mp (°C.) | |
|---|---|---|---|---|---|
| 5.001 | H | $CH_3$ | 0 | 141-143 | |
| 5.002 | $CH_3$ | $CH_3$ | 0 | 95-98 | |
| 5.003 | H | $CH_2CH_3$ | 0 | 139-140 | |
| 5.004 | $CH_3$ | $CH_2CH_3$ | 0 | | |
| 5.005 | H | $(CH_2)_2CH_3$ | 0 | | |
| 5.006 | $CH_3$ | $(CH_2)_2CH_3$ | 0 | | |
| 5.007 | H | $CH(CH_3)_2$ | 0 | | |
| 5.008 | H | $CH_2-CH=CH_2$ | 0 | | |
| 5.009 | H | $CH_2-CH=CH-CH_3$ | 0 | | |
| 5.010 | H | $CH_2-C\equiv C-CH_3$ | 0 | | |
| 5.011 | H | $(CH_2)_2Cl$ | 0 | | |
| 5.012 | $CH_3$ | $(CH_2)_2Cl$ | 0 | | |
| 5.013 | H | $(CH_2)_2OCH_3$ | 0 | | |
| 5.014 | H | $(CH_2)_2O(CH_2)_2OCH_3$ | 0 | | |
| 5.015 | H | Cyclopentyl | 0 | | |
| 5.016 | H | Cyclohexyl | 0 | | |
| 5.017 | H | $CH_2CF_3$ | 0 | | |
| 5.018 | H | $(CH_2)_2SCH_3$ | 0 | | |
| 5.019 | H | $CH_3$ | 0 | 175 decomp. | Na salt |
| 5.020 | $CH_3$ | $CH_3$ | 0 | 130 decomp. | Na salt |
| 5.021 | H | $CH_2CH_3$ | 0 | 168 decomp. | Na salt |
| 5.022 | $CH_3$ | $CH_2CH_3$ | 0 | | Na salt |
| 5.023 | H | $(CH_2)_2CH_3$ | 0 | | Na salt |
| 5.024 | H | $(CH_2)_2Cl$ | 0 | | Na salt |
| 5.025 | $CH_2-CH=CH_2$ | | 0 | 97-99 | |

TABLE 7

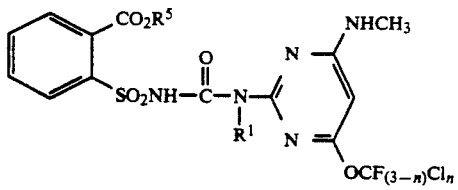

| No. | R¹ | R⁵ | n | mp (°C.) | |
|---|---|---|---|---|---|
| 7.001 | H | $CH_3$ | 0 | 188 decomp. | |
| 7.002 | $CH_3$ | $CH_3$ | 0 | | |
| 7.003 | H | $CH_2CH_3$ | 0 | 158 decomp. | |
| 7.004 | $CH_3$ | $CH_2CH_3$ | 0 | | |
| 7.005 | H | $(CH_2)_2CH_3$ | 0 | | |
| 7.006 | $CH_3$ | $(CH_2)_2CH_3$ | 0 | | |
| 7.007 | H | $CH(CH_3)_2$ | 0 | | |
| 7.008 | H | $CH_2-CH=CH_2$ | 0 | | |
| 7.009 | H | $CH_2-CH=CH-CH_3$ | 0 | | |
| 7.010 | H | $CH_2-C\equiv C-CH_3$ | 0 | | |
| 7.011 | H | $(CH_2)_2Cl$ | 0 | | |
| 7.012 | $CH_3$ | $(CH_2)_2Cl$ | 0 | | |
| 7.013 | H | $(CH_2)_2OCH_3$ | 0 | | |
| 7.014 | H | $(CH_2)_2O(CH_2)_2OCH_3$ | 0 | | |
| 7.015 | H | Cyclopentyl | 0 | | |
| 7.016 | H | Cyclohexyl | 0 | | |
| 7.017 | H | $CH_2CF_3$ | 0 | | |
| 7.018 | H | $(CH_2)_2SCH_3$ | 0 | | |
| 7.019 | H | $CH_3$ | 0 | 157 decomp. | Na salt |
| 7.020 | $CH_3$ | $CH_3$ | 0 | | Na salt |
| 7.021 | H | $CH_2CH_3$ | 0 | | Na salt |
| 7.022 | $CH_3$ | $CH_2CH_3$ | 0 | | Na salt |
| 7.023 | H | $(CH_2)_2CH_3$ | 0 | | Na salt |
| 7.024 | H | $(CH_2)_2Cl$ | 0 | | Na salt |
| 7.025 | $CH_2-CH=CH_2$ | $CH_3$ | 0 | 152-154 | |

TABLE 8

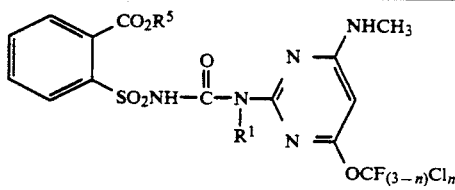

| No. | R¹ | R⁵ | n | mp (°C.) | |
|---|---|---|---|---|---|
| 8.001 | H | $CH_3$ | 1 | 186 decomp. | |
| 8.002 | $CH_3$ | $CH_3$ | 1 | | |
| 8.003 | H | $CH_2CH_3$ | 1 | | |
| 8.004 | $CH_3$ | $CH_2CH_3$ | 1 | | |
| 8.005 | H | $(CH_2)_2CH_3$ | 1 | | |
| 8.006 | $CH_3$ | $(CH_2)_2CH_3$ | 1 | | |
| 8.007 | H | $CH(CH_3)_2$ | 1 | | |
| 8.008 | H | $CH_2-CH=CH_2$ | 1 | | |
| 8.009 | H | $CH_2-CH=CH-CH_3$ | 1 | | |
| 8.010 | H | $CH_2-C\equiv C-CH_3$ | 1 | | |
| 8.011 | H | $(CH_2)_2Cl$ | 1 | | |
| 8.012 | $CH_3$ | $(CH_2)_2Cl$ | 1 | | |
| 8.013 | H | $(CH_2)_2OCH_3$ | 1 | | |
| 8.014 | H | $(CH_2)_2O(CH_2)_2OCH_3$ | 1 | | |
| 8.015 | H | Cyclopentyl | 1 | | |
| 8.016 | H | Cyclohexyl | 1 | | |
| 8.017 | H | $CH_2CF_3$ | 1 | | |
| 8.018 | H | $(CH_2)_2SCH_3$ | 1 | | |
| 8.019 | H | $CH_3$ | 1 | 163 decomp. | Na salt |
| 8.020 | $CH_3$ | $CH_3$ | 1 | | Na salt |
| 8.021 | H | $CH_2CH_3$ | 1 | | Na salt |
| 8.022 | $CH_3$ | $CH_2CH_3$ | 1 | | Na salt |
| 8.023 | H | $(CH_2)_2CH_3$ | 1 | | Na salt |
| 8.024 | H | $(CH_2)_2Cl$ | 1 | | Na salt |

TABLE 9

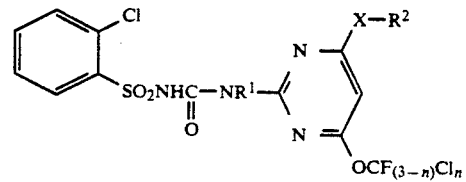

| No. | R¹ | X | R² | n | mp (°C.) | |
|---|---|---|---|---|---|---|
| 9.001 | H | — | F | 0 | 139-141 | |
| 9.002 | H | — | Cl | 0 | 181-183 | |
| 9.003 | $CH_3$ | — | F | 0 | | |
| 9.004 | $CH_3$ | — | Cl | 0 | | |
| 9.005 | H | — | F | 1 | | |
| 9.006 | H | — | Cl | 1 | | |
| 9.007 | $CH_3$ | — | F | 1 | | |
| 9.008 | $CH_3$ | — | Cl | 1 | | |
| 9.009 | H | — | F | 0 | | Na salt; |
| 9.010 | H | — | Cl | 0 | | Na salt; |
| 9.011 | H | O | $CH_3$ | 0 | 150-152 | |
| 9.012 | H | O | $CH_3$ | 1 | 142-143 | |
| 9.013 | $CH_3$ | O | $CH_3$ | 0 | | |
| 9.014 | $CH_3$ | O | $CH_3$ | 1 | | |
| 9.015 | $CH_3$ | O | $CH_3$ | 0 | | Na salt |
| 9.016 | $CH_3$ | O | $CH_3$ | 1 | | Na salt |
| 9.017 | H | NH | $CH_3$ | 0 | 177-178 | |
| 9.018 | H | NH | $CH_3$ | 1 | 183-185 | |
| 9.019 | H | $NCH_3$ | $CH_3$ | 0 | 185-188 | |
| 9.020 | H | $NCH_3$ | $CH_3$ | 1 | | |
| 9.021 | $CH_3$ | NH | $CH_3$ | 0 | | |
| 9.022 | H | O | $CH_3$ | 0 | 180 decomp. | Na salt |
| 9.023 | H | O | $CH_3$ | 1 | 184 | Na salt |

TABLE 10

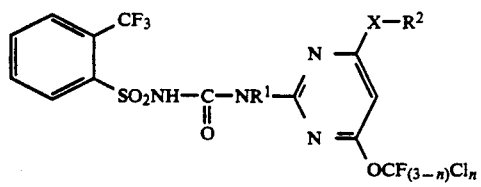

| No. | R¹ | X | R² | n | mp (°C.) | |
|---|---|---|---|---|---|---|
| 10.001 | H | — | F | 0 | | |
| 10.002 | H | — | Cl | 0 | | |
| 10.003 | H | — | F | 1 | | |
| 10.004 | H | — | Cl | 1 | | |
| 10.005 | H | O | $CH_3$ | 0 | | |
| 10.006 | H | O | $CH_3$ | 1 | | |
| 10.007 | H | NH | $CH_3$ | 0 | | |
| 10.008 | H | NH | $CH_3$ | 1 | | |
| 10.009 | $CH_3$ | NH | $CH_3$ | 0 | | |
| 10.010 | $CH_3$ | NH | $CH_3$ | 1 | | |
| 10.011 | H | O | $CH_3$ | 0 | | Na salt |
| 10.012 | H | O | $CH_3$ | 1 | 159 | Na salt |
| 10.013 | H | O | $CH_3$ | 1 | 150–153 | |
| 10.014 | H | O | $CH_3$ | 0 | 168–175 | |
| 10.015 | H | O | $CH_3$ | 0 | 146 | Na salt |
| 10.016 | H | NH | $CH_3$ | 1 | 192 | |

TABLE 11

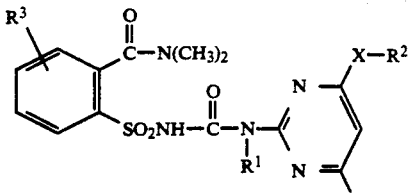

| No. | R¹ | X | R² | R³ | n | mp (°C.) |
|---|---|---|---|---|---|---|
| 11.001 | H | — | F | — | 0 | |
| 11.002 | H | — | Cl | — | 0 | |
| 11.003 | H | — | F | — | 1 | |
| 11.004 | H | — | Cl | — | 1 | |
| 11.005 | H | O | $CH_3$ | — | 0 | |
| 11.006 | H | O | $CH_3$ | 3-F | 1 | |
| 11.007 | H | NH | $CH_3$ | — | 0 | |
| 11.008 | H | NH | $CH_3$ | — | 1 | |
| 11.009 | H | O | $CH_3$ | 5-Cl | 0 | |
| 11.010 | H | O | $CH_3$ | 5-Cl | 1 | |

TABLE 12

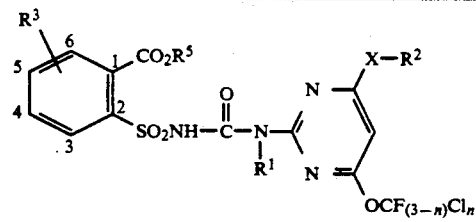

| No. | R¹ | X | R² | R³ | R⁵ | n | mp (°C.) | |
|---|---|---|---|---|---|---|---|---|
| 12.001 | H | — | F | 3-F | $CH_3$ | 0 | | |
| 12.002 | H | — | Cl | 3-F | $CH_3$ | 0 | | |
| 12.003 | H | — | F | 3-F | $CH_3$ | 1 | | |
| 12.004 | H | — | Cl | 3-F | $CH_3$ | 1 | | |
| 12.005 | H | O | $CH_3$ | 3-F | $CH_3$ | 0 | 96–98 | |
| 12.006 | H | O | $CH_3$ | 3-F | $CH_3$ | 1 | 85–86 | |
| 12.007 | H | O | $CH_3$ | 5-Cl | $CH_3$ | 0 | | |
| 12.008 | H | O | $CH_3$ | 5-Cl | $CH_3$ | 1 | | |
| 12.009 | H | — | F | 5-Cl | $CH_3$ | 0 | | |
| 12.010 | H | — | F | 5-Cl | $CH_3$ | 1 | | |
| 12.011 | H | — | Cl | 5-Cl | $CH_3$ | 0 | | |
| 12.012 | H | — | Cl | 5-Cl | $CH_3$ | 1 | | |
| 12.013 | H | — | F | 6-$CH_3$ | $CH_3$ | 0 | | |
| 12.014 | H | — | F | 6-$CH_3$ | $CH_3$ | 1 | | |
| 12.015 | H | — | Cl | 6-$CH_3$ | $CH_3$ | 0 | | |
| 12.016 | H | — | Cl | 6-$CH_3$ | $CH_3$ | 1 | | |
| 12.017 | H | O | $CH_3$ | 6-$CH_3$ | $CH_3$ | 0 | | |
| 12.018 | H | O | $CH_3$ | 6-$CH_3$ | $CH_3$ | 1 | | |
| 12.019 | H | NH | $CH_3$ | 6-$CH_3$ | $CH_3$ | 0 | | |
| 12.020 | H | NH | $CH_3$ | 6-$CH_3$ | $CH_3$ | 1 | | |
| 12.021 | $CH_3$ | NH | $CH_3$ | 6-$CH_3$ | $CH_3$ | 0 | | |
| 12.022 | H | NH | $CH_3$ | 6-$CH_3$ | $CH_3$ | 0 | | Na salt |
| 12.023 | H | — | $CF_3$ | — | $CH_3$ | 0 | 135–137 decomp. | |
| 12.024 | H | — | $CF_3$ | — | $CH_3$ | 0 | 137 decomp. | Na salt |
| 12.025 | $CH_3$ | — | $CF_3$ | — | $CH_3$ | 0 | | |
| 12.026 | H | — | $CF_3$ | — | $CH_3$ | 1 | | |
| 12.027 | H | N—$CH_3$ | $CH_3$ | — | $CH_3$ | 0 | 198 decomp. | |
| 12.028 | H | N—$CH_3$ | $CH_3$ | — | $CH_3$ | 0 | 160 decomp. | Na salt |
| 12.029 | H | N—$CH_3$ | $CH_3$ | 3-$CH_3$ | $CH_3$ | 0 | 160–165 decomp. | |
| 12.030 | H | N—$CH_3$ | $CH_3$ | 6-$CH_3$ | $CH_3$ | 1 | | |
| 12.031 | H | N—$CH_3$ | $CH_3$ | — | $CH_3$ | 1 | 185 decomp. | Na salt |
| 12.032 | H | N—$CH_3$ | $CH_3$ | — | $CH_3$ | 1 | 178 decomp. | |
| 12.033 | H | O | $C_2H_5$ | — | $CH_3$ | 0 | 141–144 | |
| 12.034 | H | O | $C_2H_5$ | — | $CH_3$ | 0 | 160 decomp. | Na salt |
| 12.035 | H | O | $C_2H_5$ | — | $CH_3$ | 1 | 127–130 | |
| 12.036 | $CH_3$ | O | $C_2H_5$ | — | $CH_3$ | 1 | | Na salt |

TABLE 12-continued

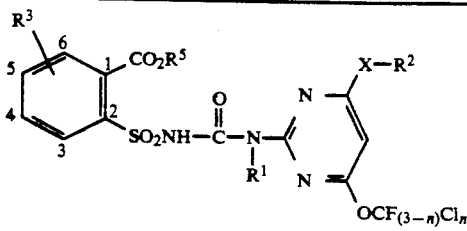

| No. | R¹ | X | R² | R³ | R⁵ | n | mp (°C.) | |
|---|---|---|---|---|---|---|---|---|
| 12.037 | H | O | $C_2H_5$ | 6-$CH_3$ | $CH_3$ | 0 | | |
| 12.038 | H | O | $C_2H_5$ | 5-Cl | $CH_3$ | 0 | 139-142 | |
| 12.039 | $CH_3$ | O | $C_2H_5$ | 5-Cl | $CH_3$ | 0 | | |
| 12.040 | H | O | $C_2H_5$ | 5-Cl | $CH_3$ | 1 | | |
| 12.041 | H | O | $CH_3$ | — | $C_2H_5$ | 0 | | |
| 12.042 | H | O | $CH_3$ | — | $C_2H_5$ | 0 | | Na salt |
| 12.043 | H | O | $CH_3$ | — | $C_2H_5$ | 1 | | |
| 12.044 | H | O | $C_2H_5$ | 4-Cl | $CH_3$ | 0 | 153 decomp. | Na salt |
| 12.045 | H | O | $CH_3$ | 6-Cl | $CH_3$ | 0 | 173-175 | |
| 12.046 | H | O | $CH_3$ | 3-Cl | $CH_3$ | 0 | | Na salt |
| 12.047 | H | O | $CH_3$ | 5-Cl | $CH_3$ | 0 | 144-145 | |
| 12.048 | H | O | $CH_3$ | 4-Cl | $CH_3$ | 0 | | Na salt |
| 12.049 | H | O | $CH_3$ | 3-Cl | $CH_3$ | 0 | 160 decomp. | |
| 12.050 | H | O | $CH_3$ | 4-Cl | $CH_3$ | 0 | 130-133 | |
| 12.051 | H | O | $C_2H_5$ | — | $CH_3$ | 1 | 155 decomp. | Na salt |
| 12.052 | H | N—$CH_3$ | $CH_3$ | 6-$CH_3$ | $CH_3$ | 0 | | |
| 12.053 | H | N—$CH_3$ | $CH_3$ | 3-$CH_3$ | $CH_3$ | 1 | 150 decomp. | |
| 12.054 | H | O | $C_2H_5$ | — | $C_2H_5$ | 0 | 139-143 decomp. | |
| 12.055 | H | NH | $CH_3$ | 3-$CH_3$ | $CH_3$ | 0 | 149-155 | |
| 12.056 | H | NH | $CH_3$ | 3-$CH_3$ | $CH_3$ | 1 | 149-155 | |
| 12.057 | H | N—$CH_3$ | $CH_3$ | 4-Cl | $CH_3$ | 0 | 165-169 | |
| 12.058 | H | N—$CH_3$ | $CH_3$ | 4-Cl | $CH_3$ | 0 | 159 decomp. | Na salt |
| 12.059 | H | N—$CH_3$ | $CH_3$ | 6-$CH_3$ | $CH_3$ | 0 | | |
| 12.060 | H | O | $C_2H_5$ | 4-Cl | $CH_3$ | 0 | 139-143 | |
| 12.061 | H | O | $C_2H_5$ | 4-Cl | $CH_3$ | 0 | 154 decomp. | Na salt |
| 12.062 | $CH_3$ | O | $CH_3$ | 4-Cl | $CH_3$ | 0 | 103-106 | |
| 12.063 | $CH_3$ | O | $CH_3$ | 4-Cl | $CH_3$ | 0 | 217 decomp. | Na salt |
| 12.064 | H | O | $CH_3$ | 3-Cl | $CH_3$ | 0 | 155 decomp. | Na salt |
| 12.065 | H | O | $CH_3$ | 4-Cl | $CH_3$ | 0 | 137 decomp. | Na salt |

TABLE 13

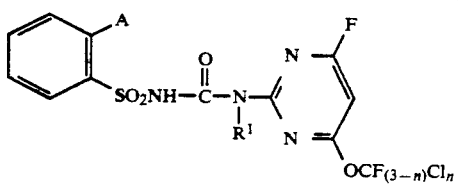

| No. | A | R¹ | n | mp (°C.) | |
|---|---|---|---|---|---|
| 13.001 | $CF_3$ | H | 1 | 179-82 | |
| 13.002 | $CF_3$ | H | 1 | 144 | Na salt |
| 13.003 | $CF_3$ | H | 0 | 162-166 | |
| 13.004 | $CF_3$ | H | 0 | 107 | Na salt |
| 13.005 | Br | H | 0 | 138-142 | |
| 13.006 | Br | H | 0 | 149 decomp. | Na salt |

USE EXAMPLES

A Herbicidal Action

The herbicidal action of the sulfonylureas of the formula I is demonstrated in greenhouse experiments.

The vessels employed were plastic flowerpots having a volume of 300 cm³ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated with the compounds, suspended or emulsified in water. The application rate for post-emergence treatment was 0.015 kg/ha.

The pots were kept in the greenhouse according to the requirements of their species, either at from 20° to 35° C., or 10° to 25° C. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plants used in the experiments were Amaranthus retroflexus, Polygonum persicaria and Triticum aestivum.

Active ingredient 6.019, applied postemergence at a rate of 0.015 kg/ha, combated unwanted broadleaved plants very well, and was tolerated by wheat.

B Bioregulatory Action

The comparative agents used in the examples were
2-chloroethyltrimethylammonium chloride (CCC) = "A"

6,7-dihydrodipyridol-(1,2-α:2',1'-c)-pyridilium ion as dibromide monohydrate salt (diquat) = "B"

Example B.1

Investigation of the Growth-Regulating Effect in Rice Seedlings

Young rice seedlings (Bahia variety) were cultivated in a nutrient solution containing varying concentrations of the active ingredients. After the plants had been grown for 6 days at 25° C. under continuous light, the active ingredient concentration was determined which reduced the length of the second leaf sheath by 50% (= $KI_{50}$).

(Details given in W. Rademacher and J. Jung, Berichte aus dem Fachgebiet Herbologie, no. 24, pp. 127–134, Hohenheim University, 1983.)

| Active ingredient no. | $KI_{50}$ (molar) |
|---|---|
| 1.001 | $8.6 \times 10^{-6}$ |
| 3.001 | $2.2 \times 10^{-6}$ |
| "A" | $1.5 \times 10^{-2}$ |

Example B.2

To determine the growth-regulating properties of the candidate compounds, test plants were grown in a soil provided with sufficient nutrients in plastic pots about 12.5 cm in diameter.

The candidate compounds were sprayed onto the plants postemergence as aqueous formulations. The growth-regulating action observed was confirmed at the end of the experiment by measuring the height of the plants. The figures obtained were compared with the growth height of the untreated plants. The compound used for comparison purposes was CCC ("A").

The reduction in growth height was also accompanied by a deeper leaf coloration. The increased chlorophyll content is indicative of an increased rate of photosynthesis, making for bigger yields.

The individual data are given in the following tables.

TABLE B.2.1

Spring barley, "Aramir" Postemergence treatment

| No. of chemical examples | Conc. mg ai/vessel | Growth height rel. |
|---|---|---|
| untreated | — | 100 |
| "A" | 0.025 | 100 |
| | 0.1 | 100 |
| | 0.38 | 96.3 |
| | 1.5 | 93.3 |
| 3.001 | 0.025 | 100 |
| | 0.1 | 100 |
| | 0.38 | 100 |
| | 1.5 | 100 |
| 5.001 | 0.025 | 56.3 |
| | 0.1 | 47.4 |
| | 0.38 | 41.5 |
| | 1.5 | 38.5 |
| 5.003 | 0.025 | 74.1 |
| | 0.1 | 59.3 |
| | 0.38 | 47.4 |
| | 1.5 | 41.5 |
| 5.019 | 0.025 | 62.2 |
| | 0.1 | 47.4 |
| | 0.38 | 41.5 |
| | 1.5 | 41.5 |
| 2.001 | 0.025 | 100 |
| | 0.1 | 100 |
| | 0.38 | 100 |
| | 1.5 | 100 |
| 1.003 | 0.025 | 100 |
| | 0.1 | 100 |
| | 0.38 | 85.9 |
| | 1.5 | 56.3 |
| 3.003 | 0.025 | 100 |
| | 0.1 | 100 |
| | 0.38 | 97.8 |
| | 1.5 | 81.5 |

TABLE B.2.2

Spring wheat, "Ralle" Postemergence treatment

| No. of chemical examples | Conc. mg ai/vessel | Growth height rel. |
|---|---|---|
| untreated | — | 100 |
| "A" | 0.025 | 100 |
| | 0.1 | 91.9 |
| | 0.38 | 87.4 |
| | 1.5 | 81.4 |
| 3.001 | 0.025 | 100 |
| | 0.1 | 100 |
| | 0.38 | 100 |
| | 1.5 | 94.9 |
| 5.001 | 0.025 | 51.2 |
| | 0.1 | 48.2 |
| | 0.38 | 48.2 |
| | 1.5 | 48.2 |
| 5.003 | 0.025 | 63.3 |
| | 0.1 | 51.2 |
| | 0.38 | 48.2 |
| | 1.5 | 48.2 |
| 5.019 | 0.025 | 51.2 |
| | 0.1 | 48.2 |
| | 0.38 | 48.2 |
| | 1.5 | 48.2 |
| 2.001 | 0.025 | 100 |
| | 0.1 | 100 |
| | 0.38 | 100 |
| | 1.5 | 100 |
| 1.003 | 0.025 | 100 |
| | 0.1 | 100 |
| | 0.38 | 93.4 |
| | 1.5 | 57.3 |
| 3.003 | 0.025 | 100 |
| | 0.1 | 100 |
| | 0.38 | 100 |
| | 1.5 | 85.9 |

TABLE B.2.3

Spring barley, "Aramir" Postemergence treatment

| No. of chemical examples | Conc. mg ai/vessel | Growth height rel. |
|---|---|---|
| untreated | — | 100 |
| "A" | 0.025 | 100 |
| | 0.1 | 100 |
| | 0.38 | 96.3 |
| | 1.5 | 93.3 |
| 1.003 | 0.025 | 100 |
| | 0.1 | 100 |
| | 0.38 | 100 |
| | 1.5 | 66.1 |
| 3.003 | 0.025 | 100 |
| | 0.1 | 100 |
| | 0.38 | 100 |

TABLE B.2.3-continued

Spring barley, "Aramir"
Postemergence treatment

| No. of chemical examples | Conc. mg ai/vessel | Growth height rel. |
|---|---|---|
|  | 1.5 | 83.3 |
| 12.032 | 0.025 | 86.0 |
|  | 0.1 | 47.6 |
|  | 0.38 | 39.7 |
|  | 1.5 | 37.0 |

TABLE B.2.4

Spring wheat, "Ralle"
Postemergence treatment

| No. of chemical examples | Conc. mg ai/vessel | Growth height rel. |
|---|---|---|
| untreated | — | 100 |
| "A" | 0.025 | 100 |
|  | 0.1 | 91.9 |
|  | 0.38 | 87.4 |
|  | 1.5 | 81.4 |
| 1.003 | 0.025 | 100 |
|  | 0.1 | 100 |
|  | 0.38 | 87.0 |
|  | 1.5 | 48.5 |
| 3.003 | 0.025 | 100 |
|  | 0.1 | 100 |
|  | 0.38 | 82.7 |
|  | 1.5 | 59.9 |
| 12.032 | 0.025 | 88.4 |
|  | 0.1 | 44.2 |
|  | 0.38 | 42.8 |
|  | 1.5 | 42.8 |

Example B.3

Young cotton plants (variety: Stoneville 825, development stage: 5 to 6 developed true leaves) were grown under greenhouse conditions (day/night temperature: 25°/18° C., relative humidity 50 to 70%), and the leaves were sprayed to runoff with aqueous formulations of the candidate compounds (with the addition of 0.15 wt % of the fatty alcohol alkoxylate Plurafac ® LF 700, based on the spray liquor). The amount of water used was equivalent to 1,000 liters/ha. The number of cast leaves was determined 6 days after application of the active ingredients and the degree of defoliation is stated in %, compared with the control. No leaves were cast from the untreated control plants.

| No. of chemical examples | Appl. rate equivalent to kg/ha | % defoliation |
|---|---|---|
| 5.003 | 0.5 | 33 |
| 5.019 | 0.5 | 32 |
| "B" | 0.5 | 47 |

We claim:
1. A substituted sulfonylurea of the formula I

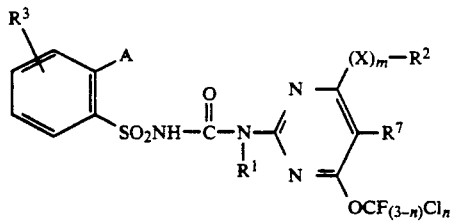

wherein
n is 1 and m is 0 or 1 and
$R^1$ is hydrogen, $C_1$-$C_4$-alkyl, $C_3$-$C_6$-alkenyl or $C_3$-$C_6$-alkynyl;
$R^2$ is halogen or trifluoromethyl when m is 0, or $C_1$-$C_4$-alkyl, $C_3$-$C_6$-alkenyl or $C_3$-$C_6$-alkynyl when m is 1, or trifluoromethyl or chlorodifluoromethyl and X is 0 or S and m is 1;
X is O, S or N—$R^4$ is hydrogen or $C_1$-$C_4$-alkyl;
$R^3$ is hydrogen, halogen, $C_1$-$C_4$-alkyl, $C_1$-$C_4$-haloalkyl or $C_1$-$C_4$-alkoxy;
A is $C_1$-$C_4$-haloalkyl, halogen or

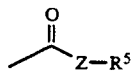

where
Z is oxygen or alkylimino $NR^6$;
$R^5$ is hydrogen, $C_1$-$C_6$-alkyl which may carry up to three of the following: halogen $C_1$-$C_4$-alkoxy, $C_1$-$C_4$-alkylthio, $C_1$-$C_4$-haloalkoxy-$C_1$-$C_4$-alkoxy, $C_1$-$C_2$-alkoxy, $C_3$-$C_7$-cycloalkyl and/or phenyl; or $C_5$-$C_7$-cycloalkyl which may carry up to three $C_1$-$C_4$-alkyl group; or $C_3$-$C_6$-alkenyl or $C_3$-$C_6$-alkenyl or $C_3$-$C_6$-alkynyl;
$R^6$ is hydrogen, $C_1$-$C_6$-alkyl, or together with $R^5$ is tetramethylene, pentamethylene, hexamethylene, ethyleneoxyethylene or ethylene-N-methyliminoethylene,
$R^7$ is hydrogen or halogen,
and environmentally tolerated salts thereof.
2. A sulfonylurea as set forth in claim 1, where the substituents have the following meanings:
$R^1$ is hydrogen or methyl;
$R^2$ is halogen or trifluoromethyl when m is 0, and methyl when m is 1;
X is O or NH;
$R^3$ is hydrogen, halogen or methyl,
A is $CO_2R^5$, where $R^5$ is $C_1$-$C_4$-alkyl;
$R^7$ is hydrogen.
3. A herbicidal composition containing an effective amount of a sulfonylurea of the formula I as set forth in claim 1, or a salt thereof, and conventional carriers therefor.
4. A process for combating the growth of unwanted plants, wherein a herbicidally effective amount of a sulfonylurea of the formula I as set forth in claim 1, or a salt thereof, is allowed to act on the plants and/or their habitat.
5. A process for regulating plant growth, wherein a growth-regulatory amount of a sulfonylurea of the formula I as set forth in claim 1, or a salt thereof, is allowed to act on the seed, the plants and/or their habitat.

* * * * *